US006476242B1

(12) United States Patent
Kingston et al.

(10) Patent No.: US 6,476,242 B1
(45) Date of Patent: Nov. 5, 2002

(54) 2-AROYL-4-ACYL PACLITAXEL (TAXOL) ANALOGS

(75) Inventors: David George Ian Kingston, Blacksburg, VA (US); Mahendra Devichand Chordia, Charlottesville, VA (US); Prakash G. Jagtap, Blacksburg, VA (US); John Kadow, Wallingford, CT (US)

(73) Assignees: Bristol-Myers Squibb Company, Princeton, NJ (US); Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 09/223,193

(22) Filed: Dec. 30, 1998

Related U.S. Application Data

(60) Provisional application No. 60/070,234, filed on Dec. 31, 1997.

(51) Int. Cl.$^7$ .............................................. C07D 305/14
(52) U.S. Cl. ....................... 549/510; 549/511
(58) Field of Search ................................ 549/510, 511

(56) References Cited

U.S. PATENT DOCUMENTS

| | | | | |
|---|---|---|---|---|
| 5,399,726 A | | 3/1995 | Holton et al. ................ | 549/510 |
| 5,587,489 A | | 12/1996 | Holton et al. ................ | 549/229 |
| 5,728,725 A | * | 3/1998 | Holton et al. ................ | 514/449 |
| 5,808,102 A | * | 9/1998 | Poss et al. ................... | 549/220 |

FOREIGN PATENT DOCUMENTS

WO     WO94/14787     7/1994

OTHER PUBLICATIONS

Kurt A. Neidigh et al. "Synthesis and Biological Evaluation of 4–Deacetoxylpaclitaxel" Tetrahedron Letters, vol. 35, No. 37, pp. 6839–6842, 1994.

Mahendra D. Chordia et al. "Synthesis and Biological Evaluation of 4–Deacetoxylpaclitaxel" Tetrahedron Letters, vol. 35, No. 37, pp. 6843–6846, 1994.

Shu–Hui Chen et al., "Novel C–4 Paclitaxel (Taxol) Analogs: Potent Antitumor Agents," Biorganic & Medicinal Chemistry Letters, vol. 5, No. 22, pp. 2741–2746, 1995.

Gunda I. Georg, Syed M. Ali, Thomas C. Boge, Apurba Datta, Lise Falborg, and Richard H. Himes, "Selective C–2 and C–4 Deacylation and Acylation of Taxol: The First Synthesis of a C–4 Substituted Taxol Analogue" Tetrahedron Letters, vol. 35, No. 48, pp. 8931–8934, 1994.

* cited by examiner

Primary Examiner—Ba K. Trinh
(74) Attorney, Agent, or Firm—Fitzpatrick, Cella, Harper & Scinto

(57) ABSTRACT

2-debenzoyl-4-deacetyl paclitaxel, antineoplastic analogs thereof and intermediates are taught, as well as the formation of the compound, analogs and intermediates. The compound, analogs and intermediates may be used to form pharmaceutical compositions having anti-neoplastic activity. Further, the compound, analogs and intermediates may be used to treat cancer when applied in an effective amount by means such as a pharmaceutical composition.

3 Claims, 3 Drawing Sheets

Scheme

Scheme 2

2-AROYL-4-ACYL PACLITAXEL (TAXOL) ANALOGS

This application claims priority under 35 U.S.C. §§119 and/or 365 to U.S. Provisional Application Serial No. 60/070,234 filed in the U.S. Patent and Trademark Office on Dec. 31, 1997 ; the entire content of which is hereby incorporated by reference.

FIELD OF INVENTION

The present invention relates to 2-debenzoyl-4-deacetyl paclitaxel, 2-debenzoyl-4-deacetyl-2,4-diacyl paclitaxel analogs thereof, and methods for making the same.

BACKGROUND OF THE INVENTION

The natural product paclitaxel (1) (Taxol®) is an effective antitumor drug with demonstrated clinical activity against breast and ovarian cancer, as well as indicated activity against non-small cell lung cancer (24, 25). Studies of use against various other cancers show promising results. Recent studies have elucidated the unique mode of action of paclitaxel, which involves abnormal polymerization of tubulin and disruption of mitosis. Taxol was first isolated and its structure reported by Wani, et al. (26).

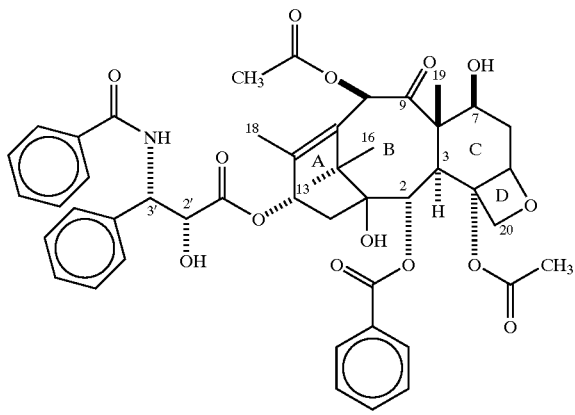

Taxol is found in the stem bark of the western yew, *Taxus brevifolia*, as well as in *T. baccata* and *T. cuspidata*. Therefore, there is a limited natural supply of paclitaxel.

Because of the limited availability of paclitaxel and the high demand due to its efficacy against various types of cancer, other derivatives and analogs of paclitaxel have been sought. The relative scarcity of such analogs in relation to their importance as potential anti-cancer agents is due to several factors, including the large size and complexity of paclitaxel compounds, the presence of multiple reactive sites and the presence of many stereospecific sites, making synthesis of even close analogs difficult.

Because it is believed that the tetracyclic taxane nucleus is an important feature in establishing the antineoplastic activity of paclitaxel and analogs thereof, it is desired to alter the ring substituents without disrupting the tetracyclic nucleus in order to develop antineoplastically active derivatives of paclitaxel. The complexity of paclitaxel and its analogs makes it difficult to selectively alter substituents.

The only disclosed preparations of taxol analogs retaining the tetracyclic taxane nucleus are those analogs modified at the C-1, C-2, C-4, C-7 and C-13 positions, and derivatives having a protecting group or a hydroxyl group at the C-10 position (27). However, it has been demonstrated that analogs with improved activity can be prepared by modifications at various functional groups, and several investigators have prepared paclitaxel analogs modified at the 2-position (1–10), at the 4-position (11–15), at the 7-position (16–19), at the 9 and 10 positions (20–21 and at the 14-position (22), among others. Baccatin III derivatives (baccatin III is the taxane core of paclitaxel) have also been prepared with substitutions at C-2 and/or C-4 (23).

In particular, analogs at the C-2 position have been prepared by Chaudhary et al. (1,3) using a phase-transfer catalyst to prepare 2-debenzoylpaclitaxel followed by reacylation with a carboxylic acid in the presence of dicyclhexylcarbodiimide (DCC) and pyrollidinopyridine (PP). Similar chemistry has more recently been reported by Georg et al. (2,5,6,13), who used potassium t-butoxide as the base and reacylated in the presence of 1,3-dicyclohexylcarbodiimide (DCC) and N,N-dimethylaminopyridine (DMAP). Nicolaou (4,7) has shown that 2-debenzoylpaclitaxels can be prepared from 10-deacetylbaccatin III by a process involving protection at C-7, oxidation at C-13, selective debenzoylation at C-2, formation of the cyclic 1,2-carbonate derivative, reaction with an aryllithium, reduction at C-13, and finally coupling of the C-13 side chain. A different route to 2-debenzoyl taxoids was developed by Pulicani et al. (8), who were able to prepare 2-debenzoyl docetaxel and certain derivatives by electrochemical reduction of docetaxel followed by reacylation with Butyllithium and an acid chloride. Yet another, albeit restricted, synthesis of certain 2-acyl paclitaxel analogs was achieved by Ojima et al. (9) and Boge et al. (10), who independently hydrogenated baccatin III to its 2-cyclohexylcarbonyl derivative, and then attached the C-13 ester side chain. 2-Debenzoylbaccatin III was prepared by Datta et al. (23) by treatment of 7,13-bis(triethylsilyl) baccatin m with potassium t-butoxide.

4-Deacetylpaclitaxel has been prepared by Neidigh et al. (11) and independently by Georg et al. (12). Neidigh et al. prepared 4-deacetylpaclitaxel by treatment of a protected paclitaxel with base under various conditions, and also by a second method in which a C-13 side chain was attached to a suitably protected 4-deacetylbaccatin III. Georg et al. prepared 4-deacetylpaclitaxel by attachment of the C-13 side chain to a protected deacetylbaccatin III. 4-Deacetylbaccatin III was also prepared by Datta et al. (23) by treatment of 7-(triethylsilyl)baccatin III with potassium t-butoxide. C-4 deacetoxypaclitaxel was prepared by Chordia et al. (15) by preparation of 2-debenzoyl-4-deacetyl paclitaxel by treatment of 2-t-butyldimethylsilyl-7-triethylsilylpaclitaxel with Triton B (an organic-soluble base) followed by formation of the cyclic 1,2-carbonate, formation of a xanthate at C-4, opening of the carbonate with phenyllithium, and deprotection.

Paclitaxels with modified C-4 acyl substituents have been prepared by Chen et al. (14), who protected 7,13-di (triethylsilyl)baccatin III at C-1 with a dimethylsilyl protecting group and then deacylated selectively at C-4 with Red-Al. Subsequent reacylation using acid chloride and lithium hexamethyldisilazide (LHDMS), followed by protecting group manipulations and reacylation at C-13 with the paclitaxel side chain (as its β-lactam derivative) yielded a range of 4-acylpaclitaxel analogs. A 4-acyl analog of paclitaxel was also prepared by Georg et al. (13), who treated 2'-t-butyldimethylsilyl-7-triethylsilylpaclitaxel with aqueous potassium t-butoxide to give a 2-debenzoyl-4-deacetyl-2'-t-butyldimethylsilyl-7-triethylsilylpaclitaxel. This compound was converted to its cyclic carbonate, acylated at C-4, and treated with phenyllithium to yield a 4-isobutyroylpaclitaxel analog.

In spite of all the work that has been done on the preparation of paclitaxel analog with C-2 and C-4 acyl substituents, no work has been reported to date on the preparation of derivatives with modified substituents at both C-2 and C-4. The preparation of such derivatives is desirable because it is anticipated that such derivatives will have antineoplastic activity, like paclitaxel itself. Further, because previous work has shown that both 2-acyl and 4-acyl analogs independently can have improved activity over paclitaxel, it is thought that some derivatives described herein will also have improved activity. It is further contemplated that the derivatives described herein will be easier to synthesize, will be more abundant, will have greater solubility and/or will have fewer side effects than paclitaxel.

The preparation of analogs of paclitaxel is an important endeavor, especially in view of paclitaxel's clinical activity and limited supply. The preparation of analogs might result in the synthesis of compounds with greater potency than paclitaxel (thus reducing the need for the drug), compounds with superior bioavailability, or compounds which are easier to synthesize than paclitaxel from readily available sources.

SUMMARY OF THE INVENTION

The present application describes paclitaxel analogs which have modified substituents at both the C-2 and C-4 positions, in particular 2-debenzoyl-2-acyl-4-deacetyl4-acyl paclitaxel analogs, as well as pro compounds, and intermediates which can be utilized in preparing these compounds.

The compounds of the present invention have antineoplastic activity and may be used to treat patients suffering from cancer, or as intermediates for making compounds which can be used to treat cancer. In a preferred embodiment, the paclitaxel analogs have improved in vivo activities for use as anticancer agents, are more soluble, and/or have fewer side effects than paclitaxel.

Compounds of the present invention include compounds having the general formula:

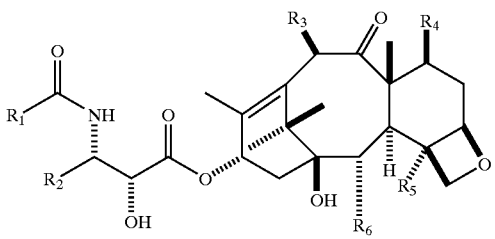

wherein $R_1$ is an aryl or substituted aryl; $R_2$ is an aryl or substituted aryl; $R_3$ is selected from the group consisting of H, OH, and $OC(O)R_a$; $R_4$ is selected from the group consisting of H, OH, oxyprotecting group (i.e. triethylsiloxy), $OR_b$, and $OC(O)R_c$, and wherein $R_a$, $R_b$, and $R_c$ are independently selected from the group consisting of alkyls, aryls, and substituted aryls; $R_5$ is selected from the group OH, $OC(O)R_d$, $OC(O)OR_e$ and $OC(S)SR_f$; and $R_6$ is selected from the group H and $OC(O)R_g$, where $R_d$, $R_e$, $R_f$ and $R_g$ are independently selected from the group consisting of alkyls, cycloalkyls, heterocycloalkyls, heterocycloaryls, alkenyls, alkynyls, aryls, and substituted aryls. As used herein, substituted aryl means an aryl independently substituted with one to five (but preferably one to three) groups selected from $C_{1-6}$ alkanoyloxy, hydroxy, halogen, $C_{1-6}$ alkyl, trifluoromethyl, $C_{1-6}$ alkoxy, aryl, heteroaryl, $C_{2-6}$ alkenyl, $C_{1-6}$ alkanoyl, nitro, amino, cyano, azido, $C_{1-6}$ alkylamino, di-$C_{1-6}$ alkylamino, and amido.

Preferred embodiments of the present invention include compounds having the formula:

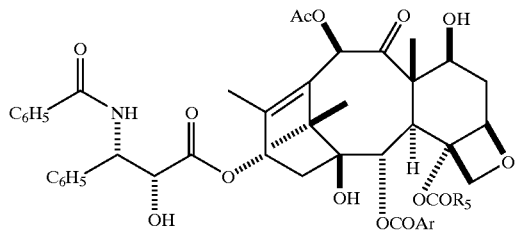

wherein Ar is a phenyl or substituted phenyl group and $R_5$ is an alkyl, cycloalkyl or an alkoxy group. Another preferred embodiment includes compounds having the formula:

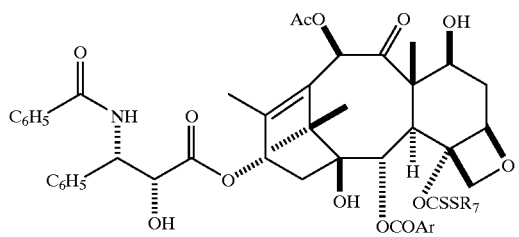

wherein Ar is a substituted phenyl and $R_7$ is an alkyl, substituted alkyl, aryl or substituted aryl group. As used herein, a substituted phenyl group may be alkyl, alkenyl, alkynyl, aryl, heteroaryl and/or may contain nitrogen, oxygen, sulfur, halogens and include, for example, lower alkoxy such as methoxy, ethoxy, butoxy; halogen such as chloro or fluoro; nitro; amino; and keto.

BRIEF DESCRIPTION OF THE FIGURES

The figures are included to more clearly demonstrate the nature of the invention.

DETAILED DESCRIPTION OF THE INVENTION

Figure 1:
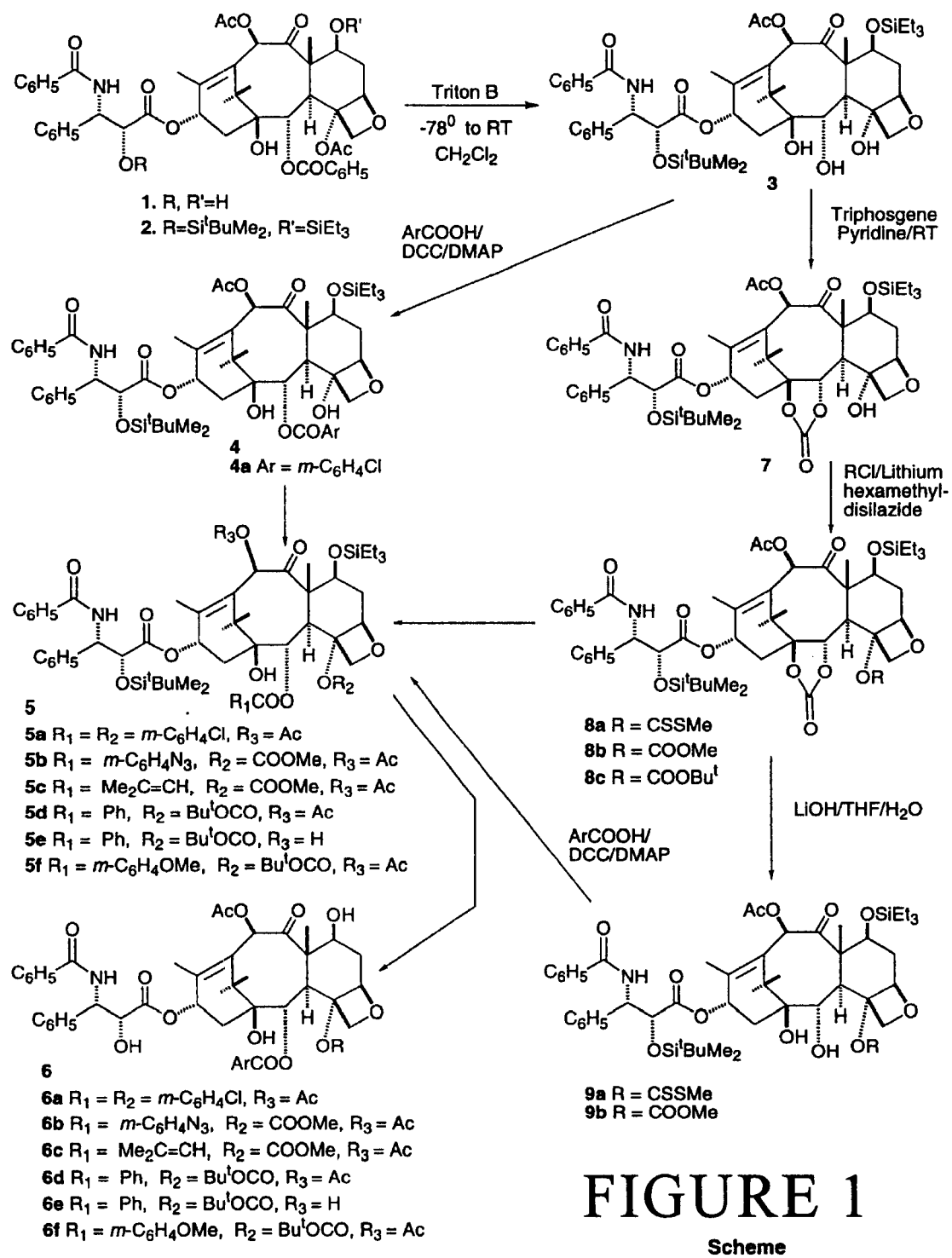
FIG. 1 is an overview of paclitaxel analogs and intermediates and the chemical reactions for converting one into another.

The present invention pertains to paclitaxel analogs having modified substituents at the C2 and C4 positions. The removal of both the benzoyl group at the C-2 position of paclitaxel and the acetyl group at the C-4 position, and the replacement of these groups with other acyl groups, yields paclitaxel analogs which are contemplated to have such characteristics as improved bioactivities, in particular, improved antineoplastic activity; improved solubility; and/or fewer side effects than paclitaxel. In addition, the paclitaxel analogs may be easier to synthesize than paclitaxel and more abundant.

In particular, paclitaxel analogs having antineoplastic activity of the formula:

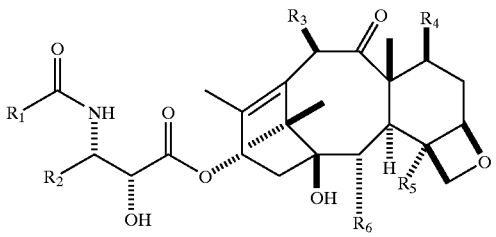

are provided, wherein $R_1$ is an aryl or substituted aryl; $R_2$ is an aryl or substituted aryl; $R_3$ is selected from the group consisting of H, OH, and $OC(O)R_a$; $R_4$ is selected from the group consisting of H, OH, oxyprotecting group (i.e. triethylsiloxy), $OR_b$, and $OC(O)R_c$, and wherein $R_a$, $R_b$, and $R_c$ are independently selected from the group consisting of alkyls, aryls, and substituted aryls; $R_5$ is selected from the group OH, $OC(O)R_d$, $OC(O)OR_e$ and $OC(S)SR_f$; and $R_6$ is selected from the group H and $OC(O)R_g$, where $R_d$, $R_e$, $R_f$ and $R_g$ are independently selected from the group consisting of alkyls, cycloalkyls, heterocycloalkyls, heterocycloaryls, alkenyls, alkynyls, aryls, and substituted aryls. As used herein, substituted aryl means an aryl independently substituted with one to five (but preferably one to three) groups selected from $C_{1-6}$ alkanoyloxy, hydroxy, halogen, $C_{1-6}$ alkyl, trifluoromethyl, $C_{1-6}$ alkoxy, aryl, heteroaryl, $C_{2-6}$ alkenyl, $C_{1-6}$ alkanoyl, nitro, amino, cyano, azido, $C_{1-6}$ alkylamino, di-$C_{1-6}$ alkylamino, and amido.

In particular, it is desirable that $R_4$ is OH and $R_3$ is $OC(O)CH_3$. It is further desirable that $R_5$ is $OC(O)R_d$ and $R_d$ is preferably an alkyl, cycloalkyl or alkoxy group. It is further preferred that, in addition to the above, $R_6$ is OC(O) $R_g$ and $R_g$ is preferably an aryl or substituted aryl group. It is even further preferred that both $R_1$ and $R_2$ be phenyl.

A further preferred analog is one wherein $R_4$ is OH, $R_3$ is $OC(O)CH_3$ and $R_5$ and $R_6$ are selected from the following combinations:

1) $R_5$ is cyclopropylcarbonyloxy and $R_6$ is selected from the group consisting of m-methoxybenzoyloxy, m-azidobenzoyloxy, m-chlorobenzoyloxy, 3,5-dichlorobenzoyloxy, 3,5-difluorobenzoyloxy, and 2,5-dimethoxybenzoyloxy;

2) $R_5$ is methoxycarbonyloxy and $R_6$ is selected from the group consisting of m-methylbenzoyloxy, m-methoxybenzoyloxy and m-chlorobenzoyloxy; and 3) $R_5$ is S-methyldithiocarboxyoxy and $R_6$ is selected from the group consisting of m-methoxybenzoyl, m-chlorobenzoyloxy and m-azidobenzoyloxy.

It is particularly preferred that the analogs of paclitaxel have a substituted benzoyloxy group at the 2-position of the B-ring and an acyloxy group or an S-alkyl or S-aryldithiocarboxyoxy group at the 4-position of the C-ring, provided that the acyloxy group is not acetyloxy. It is particularly preferred that the substituents on the benzoyloxy group be selected from hydrogen, hydroxyl, halogens, alkyls, alkoxys, nitro, cyano, azido, thiol, alkyl thiols, acyls, acyloxy, alkoxycarbonyloxys, diatomics, and linear triatomics. It is further preferred that the acyloxy group be selected from alkylcarbonyloxy, arylcarbonyloxy, substituted arylcarbonyloxy, cycloalkylcarbonyloxy, heterocycloalkylcarbonyloxy, and alkoxycarbonyloxy. The alkyl group of S-alkyldithiocarboxyoxy should be selected from alkyl, cycloalkyl, and heterocycloalkyl, while the aryl group of S-aryldithiocarboxyoxy should be selected from phenyl, substituted phenyl, and heteroaryl. As used herein, a substituted phenyl group may be alkyl, alkenyl, alkynyl, aryl, heteroaryl and/or may contain nitrogen, oxygen, sulfur, halogens and include, for example, lower alkoxy such as methoxy, ethoxy, butoxy; halogen such as chloro or fluoro; nitro; amino; and keto.

The analogs having the above general formula display an inhibitory effect on abnormal cell proliferation, and have therapeutic properties that make it possible to treat patients who have pathological conditions associated with an abnormal cell proliferation. The pathological conditions include the abnormal cellular proliferation of malignant or non-malignant cells in various tissues and/or organs, including, non-limitatively, muscle, bone and/or conjunctive tissues; the skin, brain, lungs and sexual organs; the lymphatic and/or renal system; mammary cells and/or blood cells; the liver, digestive system, and pancreas; and the thyroid and/or adrenal glands. These pathological conditions can also include psoriasis; solid tumors; ovarian, breast, brain, prostate, colon, stomach, kidney, and/or testicular cancer; Karposi's sarcoma; cholangiocarcinoma; choriocarcinoma; neuroblastoma; Wilm's tumor, Hodgkin's disease; melanomas; multiple myelomas; chronic lymphocytic leukemias; and acute or chronic granulocytic lymphomas. The paclitaxel analogs in accordance with the invention are particularly useful in the treatment of non-Hodgkin's lymphoma, multiple myeloma, melanoma, and ovarian, urothelial, oesophageal, lung, and breast cancers. The paclitaxel analogs can be utilized to prevent or delay the appearance or reappearance, or to treat these pathological conditions.

Figure 2:
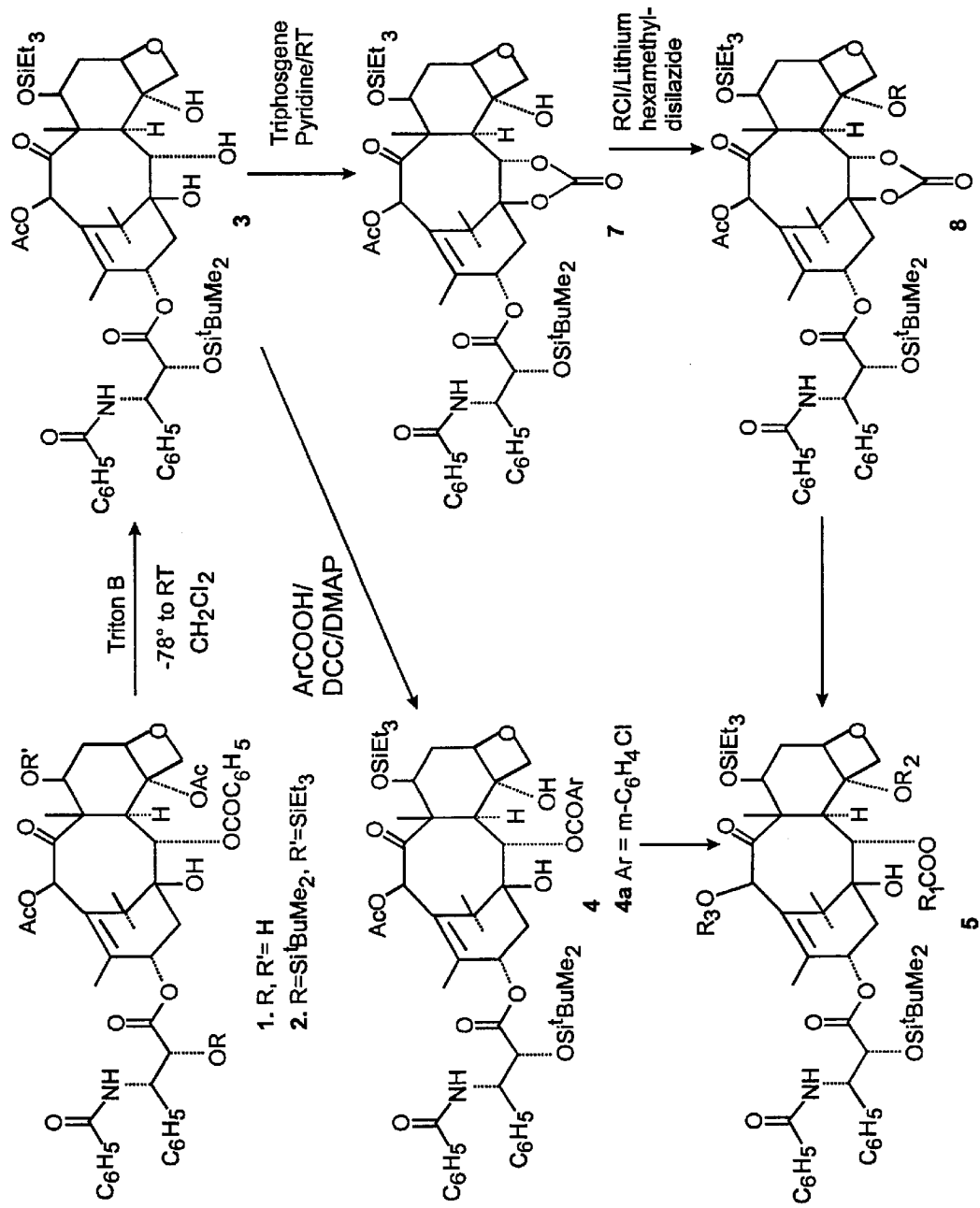
FIG. 2 shows a selection of paclitaxel analogs and intermediates and the chemical reactions for converting one into another.
Figure 3:
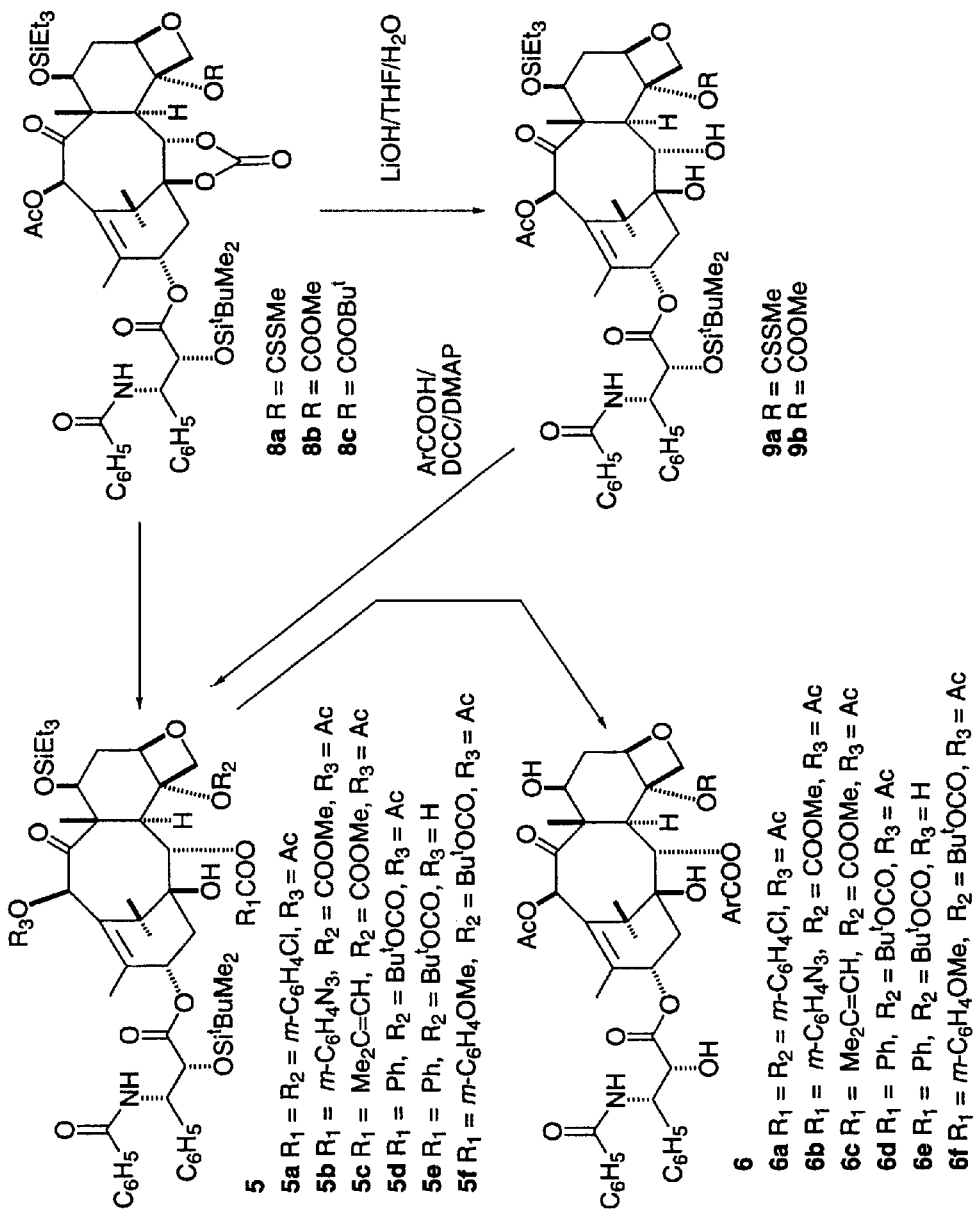
FIG. 3 shows a selection of paclitaxel analogs and intermediates and the chemical reactions for converting one into another.

The paclitaxel analogs can be made by the methods disclosed herein and techniques from the conventional organic chemistry repertoire. FIGS. 1–3, which depict processes by which compounds within the scope of the above general formula can be made, are only shown for the purpose of illustration and are not to be construed as limiting the processes to make the compounds by any other methods.

The present invention provides analogs useful as active agents in effecting an antitumor or antineoplastic effect in a tumor-bearing host. These analogs or their pharmaceutically acceptable salts can be compounded into pharmaceutical formulations for administration to cancer patients. Such formulations will comprise one or more of the active agents of the present invention in combination with pharmaceutically acceptable excipients and/or adjuvants. Contemplated routes of administration are parenteral and oral, though other acceptable means of administration will be obvious to those of ordinary skill in the art.

The present invention further provides a method for inhibiting, reducing, or eliminating tumors comprising administering to a mammalian, especially a human, tumor bearing host an antitumor effective amount of an analog of the general formula shown above.

For treating a variety of tumors, the analogs of the present invention are contemplated to be used in a manner similar to that of paclitaxel, see e.g. Physician's Desk Reference, 49th Edition, Medical Economics, p 682, 1995. The dosage, mode and schedule of administration for the analogs of this invention are not particularly restricted; an oncologist skilled in the art of cancer treatment will be able to ascertain, without undue experimentation, an appropriate treatment protocol for administering the analogs of the present invention. Thus the analogs will be administered via any suitable route of administration, in particular, parenterally or orally. Parenteral administration includes intravenous, intraperitoneal, intramuscular, and subcutaneous administration.

The doses utilized to implement the methods of the present invention will be similar to those used in administering paclitaxel, taking into account the relative activity of the analogs described herein. It is expected that one of ordinary skill in the art will be able to discern suitable anti-tumor effective doses and regimens for the efficacious administration of the present paclitaxel analogs. It will be understood that such doses vary, depending on the type of administration, the particular product selected, and the profile and particular characteristics of the patient to be treated. The desired doses will be those that are therapeutically effective for the treatment of disorders caused by abnormal cell proliferation. The analogs of the present invention can be administered as often as necessary in order to obtain the desired therapeutic effect. Some patients may respond rapidly to relatively high or low doses, and then require mild maintenance or no maintenance dose at all. When administered via IV, the dosage may be, for example, in the range of about 20 to about 500 mg/m$^2$ over 1 to 100 hours. Orally, the dosage may be in the range of 5–1000 mg/kg/day of body weight. The actual dose used will vary according to the particular composition formulated, the route of administration, and the particular site, host and type of tumor being treated. Many factors that modify the action of the drug will be taken into account in determining the dosage including age, weight, sex, diet and the physical condition of the patient.

The present invention also provides pharmaceutical formulations (compositions) containing an antitumor effective amount of the paclitaxel analogs of the above general formula in combination with one or more pharmaceutically acceptable carriers, excipients, diluents or adjuvants. The compositions can be prepared in accordance with conventional methods. For example, paclitaxel is formulated for parenteral administration in polyethoxylated castor oil (Cremophor®). Examples of formulating paclitaxel or derivatives thereof are also found in, for example, U.S. Pat. Nos. 4,960,790 and 4,814,470, and such examples can be followed to formulate the compounds of this invention. For example, analogs of the general formula might be formulated in the form of tablets, pills, powder mixtures, capsules, injectables, storage stable solutions, suppositories, emulsions, dispersions, food premix, and in other suitable forms. They might also be manufactured in the form of sterile solid compositions, for example, freeze dried (lyophilized) and, if desired, combined with other pharmaceutically acceptable excipients. Such solid compositions can be reconstituted with sterile water, physiological saline, or a mixture of water and an organic solvent, such as propylene glycol, ethanol, and the like, or some other sterile injectable medium immediately before use in parenteral administration.

Typical of pharmaceutically acceptable carriers are, for example, manitol, urea, dextrans, lactose, potato and maize starches, magnesium stearate, talc, vegetable oils, polyalkylene glycols, ethyl cellulose, poly(vinylpyrrolidone), calcium carbonate, ethyl oleate, isopropyl myristate, benzyl benzoate, sodium carbonate, gelatin, potassium carbonate, silicic acid. The pharmaceutical preparation may also contain nontoxic auxiliary substances such as emulsifying, preserving, wetting agents, and the like as for example, sorbitan monolaurate, triethanolamine oleate, polyoxyethylene monostearate, glyceryl tripalmitate, dioctyl sodium sulfosuccinate, and the like.

It is further desirable to formulate intermediates of paclitaxel analogs for further study on the effectiveness of paclitaxel derivatives against cancer and other diseases and to facilitate the formation of various paclitaxel analogs. One preferred intermediate is derived from the following paclitaxel analog, which can be made by reacting 2'-t-butyldimethylsilyl-7-triethylsilylpaclitaxel with Triton B in dichloromethane:

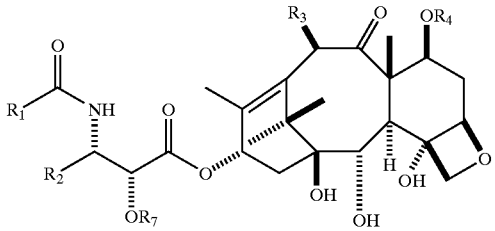

wherein the analog has a protecting group at each of the positions C-2' and C-7 and having OH groups at positions C-2 and C-4, and wherein $R_1$ and $R_2$ are independently selected from the group consisting of aryl, substituted aryl and heteroaryl; $R_3$ is hydroxy or acyloxy; $R_4$ is trialkylsilyl; and $R_7$ is trialkylsilyl. The intermediate preferably is of a structure such that $R_1$ and $R_2$ are phenyl, $R_3$ is acetoxy, $R_4$ is triethylsilyl, and $R_7$ is t-butyldimethylsilyl.

A second preferred intermediate is derived from the following paclitaxel analog:

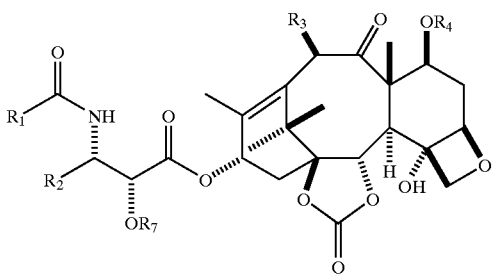

wherein $R_1$ and $R_2$ are independently selected from the group consisting of aryl, substituted aryl or heteroaryl; $R_3$ is hydroxy or acyloxy; $R_4$ is trialkylsilyl; and $R_7$ is trialkylsilyl. The intermediate preferably is of a structure such that $R_1$ and $R_2$ are phenyl, $R_3$ is acetoxy, $R_4$ is triethylsilyl, and $R_7$ is t-butyldimethylsilyl. The second intermediate can be formed by reacting 2'-t-butyldimethylsilyl-2-debenzoyl-4-deacetyl-7-triethylsilylpaclitaxel with carbonyldiimidazole or triphosgene.

A third intermediate is derived from the following paclitaxel analog:

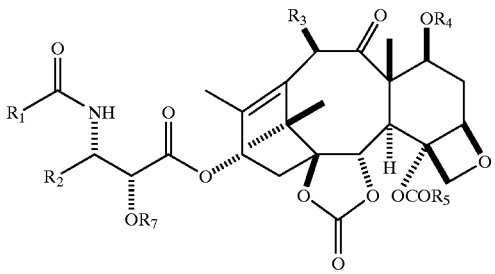

wherein $R_1$ and $R_2$ are independently selected from the group consisting of aryl, substituted aryl or heteroaryl; $R_3$ is hydroxy or acyloxy; $R_4$ is trialkylsilyl; $R_7$ is trialkylsilyl; and $R_5$ is selected from the group consisting of alkyls, cycloalkyls, heterocycloalkyls, heterocycloaryls, alkenyls, alkynyls, aryls, and substituted aryls. It is preferred that the intermediate have a structure such that $R_1$ and $R_2$ are phenyl, $R_3$ is acetoxy, $R_4$ is triethylsilyl, and $R_7$ is t-butyldimethylsilyl. The third intermediate may be formed by reacting the second intermediate with a carboxylic acid in the presence of DCC and DMAP.

A fourth intermediate is derived from the following paclitaxel analog:

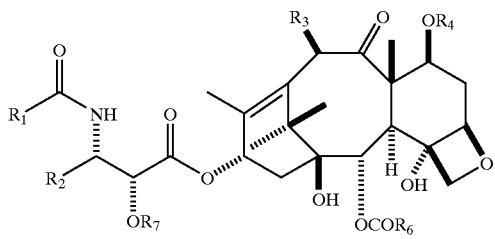

wherein $R_1$ and $R_2$ are independently selected from the group consisting of aryl, substituted aryl or heteroaryl; $R_3$ is hydroxy or acyloxy; $R_4$ is trialkylsilyl; $R_7$ is trialkylsilyl; and $R_6$ is selected from alkyls, cycloalkyls, heterocycloalkyls, heterocycloaryls, alkenyls, alkynyls, aryls, and substituted aryls. The intermediate preferably has a structure such that $R_1$ and $R_2$ are phenyl, $R_3$ is acetoxy, $R_4$ is triethylsilyl, and $R_7$ is t-butyldimethylsilyl. This intermediate may be synthesized by reacting 2'-t-butyldimethylsilyl-2-debenzoyl-4-deacetyl-7-triethylsilylpaclitaxel with a carboxylic acid ($R_6$COOH) in the presence of DCC and DMAP.

A fifth intermediate may be formed from the paclitaxel analog compound having the composition:

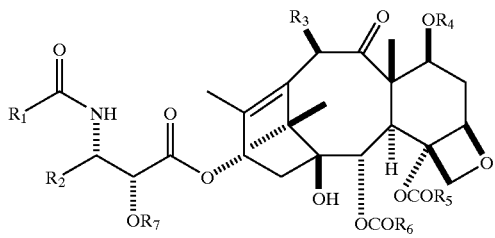

wherein $R_1$ and $R_2$ are independently selected from the group consisting of aryl, substituted aryl or heteroaryl; $R_3$ is hydroxy or acyloxy; $R_4$ is trialkylsilyl; $R_5$ and $R_6$ are independently selected from the group consisting of alkyls, cycloalkyls, heterocycloalkyls, heterocycloaryls, alkenyls, alkynyls, aryls, and substituted aryls; and $R_7$ is trialkylsilyl. The intermediate preferably is of the structure wherein $R_1$ and $R_2$ are phenyl, $R_3$ is acetoxy, $R_4$ is triethylsilyl, and $R_7$ is t-butyldimethylsilyl. This intermediate may be synthesized by reacting 2'-t-butyldimethylsilyl-4-deacetyl-7-triethylsilylpaclitaxel with a carboxylic acid under forcing conditions in the presence of DCC and DMAP. Alternatively, this intermediate may be synthesized by reacting the third intermediate with lithium hydroxide followed by a carboxylic acid ($R_6$COOH), DCC and DMAP.

Two different methods have been developed for the synthesis of paclitaxel analogs of the desired type.

In the first method, as illustrated in FIG. 1, paclitaxel (1) is converted to its 2'-t-butyldimethylsilyl-7-triethylsilyl derivative 2 by treatment in succession with t-butyldimethylsilyl chloride/imidazole and then with triethylsilyl chloride/pyridine. Treatment of 2 with Triton B under carefully defined conditions (−78° to −10°, $CH_2Cl_2$) gave the triol 3 (2-debenzoyl-4-deacetyl-2'-t-butyldimethylsilyl-7-triethylsilylpaclitaxel) as a key intermediate. This intermediate has been prepared previously by us (15) and by Georg (13).

Treatment of the triol 3 with a desired substituted benzoic acid, such as m-methoxybenzoic acid, in the presence of DCC and DMAP, yielded the 2-acyl derivative 4. If the conditions are adjusted appropriately, the diacyl derivative 5, where R=Ar, can be prepared in good yield. However, treatment of 4 with excess carboxylic acid in the presence of DCC and DMAP yields the diacyl derivative 5 in modest yield, where Ar and R are independently selectable depending on the carboxylic acids used in the two acylation steps.

Deprotection of 5 under standard conditions (dilute HCl or HF/pyridine) yielded the diacyl paclitaxel analog 6.

In the second method, as also illustrated in FIG. 1, paclitaxel (1) was converted as before to the triol 3. This triol was then protected as the cyclic carbonate derivative 7 by treatment with carbonyl diimidazole or triphosgene. Cyclic carbonates of a related type have been prepared by Holton (U.S. Pat. No. 5,399,726) and by Nicolaou (4,7); the carbonate 7 has previously been prepared by us (15) and by Georg (13).

Acylation of the carbonate 7 with a selected acyl chloride in the presence of lithium hexamethyldisilazide gave the 4-acyl analog 8. This analog could be converted to the diprotected 2-acyl-4-acylpaclitaxel 5 in two ways. In the first method, 8 was hydrolysed by lithium hydroxide in THF/$H_2O$ to yield the diol 9, which could be acylated under our standard conditions (ArCOOH/DCC/DMAP) to give the diacyl analog 5. In the second method, treatment of 8 with an aryllithium reagent converted it directly to 5, as previously observed by Holton (U.S. Pat. No. 5,399,726), by Nicolaou (4,7), by ourselves (15), and by Georg (13). Deprotection of 5 as previously described then yielded the desired 2,4-diacylpaclitaxel analog 6.

Following the procedures described above, together with procedures that are common in the art, such as those described in Klein et al., *J. Med. Chem.*, 38, pp 1482–1492 (1995), other analogs within the scope of this invention can be synthesized, such as those shown in the table below.

TABLE 1

2-AROYL-4-ACYL PACLITAXEL ANALOGS

| Number | BMS # | Brief Sample Name | Tubulin Data | anal/PT | HCT116 | 116/VM46 | anal/PT | R/S ratio |
|---|---|---|---|---|---|---|---|---|
|  | 181339 | paclitaxel (PT) | 6.9 +/− 1.1 | 1 | 2 | 203 | N.A. | 101 |
| MC-134-61 | 198235 | 2-(m-methoxybenzoyl)-4-MeOCO-PT |  | 0.9 | 6.7, 4.4 | 867, >87 |  | 129 |
| MC-134-45 | 198244 | 2-(m-methoxybz)-4-cyclopropylCO-PT |  | 1.3 | 2 | 40 |  | 20 |
| MC-134-68 | 198245 | 2-(m-methylbenzoyl)-4-MeOCO-PT |  | 0.8 | 2.1 | 44 |  | 21 |
| MC-134-180 | 198336 | 2-m-azido-4-cyclopropylCO-PT |  |  |  |  |  |  |
| MC-134-91 | 198336 | 2-m-azido-4-cyclopropylCO-PT |  | 0.08 | 2.7, 1.1 | 28, <16 |  | 10.4 |
| MC-134-191 | 198337 | 2-m-chloro-4-cyclopropylCO-PT |  |  |  |  |  |  |
| MC-134-92 | 198337 | 2-m-chloro-4-cyclopropylCO-PT |  | 0.06 | 1.7, 1.1 | 30, <16 |  | 18 |

TABLE 1-continued

2-AROYL-4-ACYL PACLITAXEL ANALOGS

| Number | BMS # | Brief Sample Name | Tubulin Data | anal/PT | HCT116 | 116/VM46 | anal/PT | R/S ratio |
|---|---|---|---|---|---|---|---|---|
| MC-134-100 | 198638 | 2-m-chloro-4-MeOCO-PT | 1.7 +/− 0.2 | 0.4 | 2.2 | 82 | | 37 |
| MC-134-239 | 200333 | 2-(m-azidobenzoyl-4-xanthyl)PT | 250 +/− 0 | 42 | 0.0168 | 0.1348 | 11.02 | 8.03 |
| MC-134-238 | 200334 | 2-(m-chlorobenzoyl-4-xanthyl)PT | 21 +/− 5.9 | 3.5 | 0.0057 | 0.0586 | 3.72 | 10.34 |
| MC-134-229 | 200335 | 2-(m-methoxybenzoyl-4-xanthyl)PT | 52 +/− 41 | 8.9 | 0.0047 | 0.0532 | 3.08 | 11.32 |
| MC-134-248 | 200532 | 2-(2,4-difluorobz)-4-cyclopropylCO-PT | 1.3 +/− 0.1 | 0.2 | 0.0021 | 0.0082 | 1.03 | 3.86 |
| MC-134-250 | 200541 | 2-(2,5-dimethoxybz)-4-cyclopropylCO-PT | 3.4 +/− 0.8 | 0.5 | 0.0018 | 0.0451 | 0.78 | 25.06 |
| MC-134-247 | 200545 | 2-(2,4-dichlorobz)-4-cyclopropylCO-PT | 5.4 +/− 2.9 | 0.7 | 0.0025 | 0.0766 | 1.09 | 30.64 |
| MC-134-277 | 200750 | 2-(m-Cl-benzoyl)-4-(m-Cl-benzoyl)PT | 420 +/− 140 | 144 | 2427 | 2461 | | |
| PJ-143-261 | 242855 | 2-(m-Azidobenzoyl)-4-MeOCO-PT | | | | | | |
| PJ-143-263 | 242857 | 2-(3,3-Dimethylacryloyl)-4-MeOCO-PT | | | | | | |
| PJ-143-264 | 242861 | 2-(m-MeO-benzoyl)-4-t-BuOCO-PT | | | | | | |

EXAMPLES

MATERIALS AND METHODS

General Methods

Specific reaction conditions are described in more detail in the following non-limiting examples. Certain methods used herein are generally described in the *Journal of Organic Chemistry*, 51, pp. 797–802 (1986) The term "standard workup" or "usual workup" used herein includes extraction with a suitable solvent (usually ethyl acetate or methylene chloride), washing the extract with water, drying over magnesium sulfate or sodium sulfate, and evaporation in vacuo. All technical and scientific terms used herein have the same meaning as commonly understood by one of ordinary skill in the art.

All chemicals were procured from Aldrich Chemical Company and used without further purification. AU anhydrous reactions were performed under argon. THF was dried over sodium/benzophenone. All reactions were monitored by TLC (silicagel, GF) and analyzed with UV light and developed with vanillin spray. $^1$H NMR and $^{13}$C spectra were obtained in CDCl$_3$ at 270 and 400 MHZ for proton spectra and assigned primarily by comparison of chemical shifts and coupling constants with those of related compounds and by appropriate 2D NMR techniques. Coupling constants are reported in Hz. $^{13}$C spectra were assigned using HETCOR and DEPT spectra. $^1$H NMR spectra showed the presence of traces of ethyl acetate; paclitaxel and its derivative retain ethylacetate very tightly, and it cannot be removed completely even on prolonged treatment in vacuo at 38° C. Exact mass measurements were performed at the Midwest Center for Mass Spectrometry, an NSF Regional Instrumentation Facility. IUPAC nomenclature for paclitaxel derivatives is used for title compounds.

2'-O-tert-Butyldimethylsilyl-7-O-triethylsilylpaclitaxel (2)

To a stirred solution of paclitaxel 1 (270 mg, 0.316 mmol) in 2.5 mL anhydrous DMF, imidazole (107 mg, 1.58 mmol) and tert-butyldimethylsilyl chloride (238 mg, 1.58 mmol) were added. The solution was heated at 60° C. for 2 hours. The mixture was cooled to room temperature, and additional amounts of imidazole (107 mg, 1.58 mmol) and triethylsilyl chloride (150 μL, 1.34 mmol) were added. After stirring at room temperature for one hour, the reaction mixture was diluted with EtOAc and washed successively with water and brine. Drying of the organic layer over Na$_2$SO$_4$ and evaporation under reduced pressure yielded crude material. Purification of the crude material by column chromatography over silica gel (EtOAc:hexanes, 1:2) gave 2'-O-tert-butyldimethylsilyl-7-O-triethylsilylpaclitaxel (2) (325 mg, 95%) as an amorphous solid having the following characteristics: m.p. 130–131°; $^1$H-NMR δ−0.20 (s, 3H, SiCH$_3$), −0.02 (s, 3H, SiCH$_3$), 0.62 (q, J=7.8, 6H, SiCH$_2$), 0.79 (s, 9H, tBu), 0.92 (t, J=7.8, 9H, SiCH$_2$CH$_3$), 1.17 (s, 3H, C-16CH$_3$), 1.21 (s, 3H, C-17CH$_3$), 1.70 (s, 3H, C-19CH$_3$), 2.02 (bs, 3H, C-18CH$_3$), 2.16 (s, 3H, C-10 OAc), 2.40 (m, 1H, C-14H), 2.55 (m, 1H, C-6H), 2.58 (s, 3H, C-4OAc), 3.83 (d, J=7.0, 1H, C-3H), 4.19 (d, J=8.3, 1H, C-20H), 4.30 (d, J=8.3, 1H, C-20H), 4.48 (dd, J=9.4, 6.6, 1H, C-7H), 4.67 (d, J=2.1, 1H, C-2'H), 4.94 (bd, J=8.8, 1H, C-5H), 5.69 (d, J=7.0, 1H, C-2H), 5.74 (dd, J=9.0, 2.1, 1H, C-3'H), 6.26 (bt, 1H, C-13H), 6.45 (s, 1H, C-10H), 7.10 (d, J=8.9, 1H, C-3'NH), 7.30–7.60 (m, 11H, ArH) 7.74 (dd, J=8.5, 1.5, 2H, C-3'NBz orthoH), 8.13 (dd, J=8.5, 1.4, 2H, C-2-OBz orthoH); $^{13}$C-NMR δ−5.86, −5.20, 5.27, 6.73, 10.11, 14.24, 18.11, 20.85, 21.50, 23.10, 25.49, 26.54, 35.55, 37.21, 43.31, 46.64, 55.63, 58.39, 71.36, 72.19, 74.92, 74.95, 75.10, 76.55, 78.82, 81.17, 84.22, 126.40, 126.97, 127.92, 128.68, 128.70, 128.71, 129.19, 130.20, 131.76, 133.60, 133.66, 134.03, 138.26, 140.14, 166.88, 167.03, 169.28, 170.13, 171.38, 201.67; fabms m/z (rel int.) [M+H]$^+$ 1104 (5), 705 (3), 422 (40), 354 (12), 105 (100); HRFABMS m/z [M+Na—H]$^+$ 1104.4936 (C$_{59}$H$_{79}$NO$_{14}$Si$_2$Na requires 1104.4937).

2'-O-tert-ButyldimethylsilI-7-O-triethylsilyl-2-debenzoyl-4-deacetylpaclitaxel (3)

To a solution of compound 2 (110.4, 0.1 mmol) in anhydrous CH$_2$Cl$_2$ was added benzyltrimethyl ammonium hydroxide (TritonB, 100 μL, 40% w/w solution in methanol) at −78° C. The reaction mixture was stirred at −78° C. for 5 minutes and the cooling bath was removed to allow the reaction mixture to warm to −10° (ethylene glycol; dry ice bath). The mixture was stirred at −10° C. for one hour, and the progress of the reaction was monitored with TLC. The TLC analysis revealed first formation of more polar 2-debenzoyl compound (Rf 0.3), that further converted to nonpolar 2-debenzoyl-4-deacetyl compound (Rf 0.5). After completion of the reaction, the mixture was diluted with cold CH$_2$Cl$_2$ (−40°) and quenched with 5 mL 0. 1N HCI. The organic layer was separated by washing successively with water, dilute NaHCO$_3$ and brine, and drying over Na$_2$SO$_4$. Concentration under reduced pressure gave a crude residue that was purified by PTLC (silica gel, 1000 m, ethylacetate:hexanes, 2:3) to yield compound 3 (60.7 mg, 65%).

Aroylation of 2'-O-tert-Butyldimethylsilyl-7-O-triethylsilyl-2-debezneoyl-4-deacetylpaclitaxel (5a)

To a mixture of m-chlorobenzoic acid (26.6 mg, 0.16 mmol), DCC (39.6 mg, 0.18 mmol), 4-pyrrolidino pyridine (1.0 mg, 0.006 mmol) in dry toluene (0.3 mL) was added 2-debenzoyl-4-deacetyl-4-acyl-2'-tert-butyl-7-triethylsilylpaclitaxel (9) (20.0 mg, 0.02 mmol). The mixture was stirred at room temperature for 10 hours. TLC analysis indicated formation of two new compounds, both of which were non polar (Rf 0.5 and 0.4) as compared to the starting material (Rf 0.3). The reaction mixture was then diluted with EtOAc hexane (1:1, 10mL) and filtered through a pad of silica gel and celite. This pad was further washed with EtOAc (2 mL). The filtrate was concentrated on a rotary evaporator to give a crude product. Further purification using preparative TLC (silica gel; 500 m, hexane:EtOAc; 2:1) gave the less polar spot as the 2,4-di-(m-chlorobenzoyl)-paclitaxel derivative 5a (6.0 mg, 23%) and the more polar spot as 2-(m-chlorobenzoyl)-2'-O-tert-butyldimethylsilyl-7-O-triethylsilypaclitaxel (12.5 mg, 54%).

$^1$H NMR of 2-(m-chlorobenzoyl)-4-deacetyl-2'-O-tert-butyldimethylsilyl-7-O-triethylsilyl-paclitaxel (4a): δ 0.23 (s, 3H, SiCH$_3$), 0.07 (s, 3H, SiCH$_3$), 0.60 (q, J=7.8, 6H, SiCH$_2$), 0.83 (s, 9H, tBu), 0.93 (t, J=7.8, 9H, SiCH$_2$CH$_3$), 1.06 (s, 3H, C-16CH$_3$), 1.23 (s, 3H, C-17CH$_3$), 1.58 (s, 3H, C-19CH$_3$), 2.00 (m, 1H,C-6H), 2.16 (bs, 3H, C-18CH$_3$), 2.19 (s, 3H, C-10 Oac), 2.30 (dd, 1H, C-14H), 2.53 (m, 1H, C-6H), 2.79 (dd, 1H, C-14H), 3.45 (d, J=6.0, 1H, C-3H), 4.16 (m, 2H, C-7H and C-20H), 4.28 (d, J=8.3, 1H, C-20H), 4.56 (d, J=1.2, 1H, C-2'H), 4.82 (s, 1H, C-4 OH), 4.91 (dd, J=2.1, 7.0, 1H, C-5H), 5.70 (d, J=6.0, 1H, C-2H), 5.91 (bt, 1H, C-13H), 6.06 (bd, 1H, C-3'H), 6.48 (s, 1H, C-1OH), 7.60 (t, J=8.0, 1H, ArH), 7.30–7.66 (m, ArH), 8.14 (bs, 1H, ArH), 8.19 (dt, 1H, ArH); $^{13}$C-NMR δ −5.86, −5.51, 5.27, 6.75, 9.84, 16.10, 18.27, 18.90, 20.92, 25.52, 27.47, 35.08, 37.51, 43.02, 51.58, 55.03, 58.91, 71.57, 72.63, 74.34, 75.32, 75.52, 75.60, 77.20, 81.06, 87.55, 126.83, 126.99, 127.93, 128.34, 128.57, 128.81, 130.01, 130.36, 130.68, 131.80, 133.47, 134.66, 134.71, 136.00, 138.87, 139.24, 166.21, 167.80, 169.47, 170.20, 202.25.

$^1$H and $^{13}$C NMR spectrum of 2-(m-Chlorobenzoyl)-4-(m-chlorbenzoyl)-2-O-tert-butyldimethyl silyl-7-O-triethylsilylpaclitaxel (5a): $^1$H-NMR δ −0.11 (s, 3H, SiCH$_3$), 0.03 (s, 3H, SiCH$_3$), 0.62 (q, J=7.8, 6H, SiCH$_2$), 0.84 (s, 9H, tBu), 0.93 (t, J=7.8, 9H, SiCH$_2$CH$_3$), 1.15 (s, 3H, C-16CH$_3$), 1.23 (s, 3H, C-17CH$_3$), 1.74 (s, 3H, C-19CH$_3$), 1.89 (bs, 3H, C-18CH$_3$), 1.95 (m, 1H, C-6H), 2.21 (dd, 1H, C-14 OAc), 2.41 (dd, 1H, C-14H), 2.56 (m, 1H, C-6H), 2.92 (d, 1H, C-2'H), 4.10(d, 1H, C-3H), 4.32 (d, J=8.3, 1H, C-20H), 4.46 (d, J=8.3, 1H, C-20H), 4.62 (dd, J=9.4, 6.6, 1H, C-7H), 4.91 (d, J=2.1, 1H, C-3'-H), 4.97 (dd, J=8.8, 1H, C-5H), 5.78 (d, J=7.0, 1H, C-2H), 5.87 (bt, 1H, C-13H), 6.51 (s, 1H, C-10H), 6.79 (d, J=8.9, 1H, C-3'NH), 6.98 (d, 2H, ArH), 7.30–7.66 (m, 11H, ArH), 8.13 (dt, J=8.5, 1.4, 2H, ArH), 8.17 (dt, 2H, ArH), 8.21 (dt, 2H, ArH); $^{13}$C-NMR δ −5.31, −4.90, 5.27, 6.75, 10.16, 14.07, 18.13, 20.83, 21.80, 25.59, 26.44, 35.70, 37.20, 43.44, 46.61, 55.47, 58.42, 71.99, 72.72, 73.92, 74.87, 75.61, 76.61, 78.65, 82.62, 84.49, 126.80, 127.20, 127.65, 127.81, 128.23, 128.43, 128.64, 129.57, 129.82, 130.21, 130.24, 131.40, 131.61, 131.89, 133.30, 133.70, 134.14, 134.22, 134.78, 134.99, 138.05, 140.73, 164.47, 165.62, 166.97, 169.22, 172.43, 201.62.

2'-tert-Butyldimethysilyl-4-deacetyl-2-debenzoyl-7-triethysilyl-paclitaxel 1,2-Carbonate (7)

Compound 3 (93.5 mg, 0.1 mmol)) was dissolved in dry CH$_2$Cl$_2$ (0.3 mL) and pyridine (0.3 mL). To this solution triphosgene (45.0 mg, 0.15 mmol) was added and the mixture was stirred at room temperature for 4 hours. The reaction mixture was then diluted with CH$_2$Cl$_2$ and washed with 0.1 N HCl, water and brine. The organic layer was dried over Na$_2$SO$_4$ and concentrated under reduced pressure to give a crude product that was purified by PTLC (silica gel, 1000 m, ethylacetate:hexanes, 1:3) to yield compound 7 (51.7 mg, 83%). FABMS m/z (rel int.) [M+H]$^+$ 962.4(8), 904(3), 621(2), 400(90), 354(75), 105 (100); HRFABMS m/z [M+H]$^+$ 962.4512 (C$_{51}$H$_{71}$NO$_{13}$Si$_2$Na requires 961.4464).

2'-tert-Butyldimethysilyl-7-triethylsilyl-4-acylpaclitaxel 1,2-Carbonate Derivatives (8)

To a cooled (−78° C., acetone, dry ice) solution of compound 7 (32.0 mg, 0.033 mmol) in freshly distilled anhydrous THF (0.5 mL) was added lithium hexamethyldisilamide (0.125 mmol) via syringe under argon. The mixture was stirred at −78° C. for 15 minutes. The respective electrophile (acid chloride or chloroformate, 0.250 mmol) was added via syringe and the mixture was further stirred for 15 minutes at −78° C. Then the reaction mixture was allowed to warm to 0° C. and diluted with EtOAc (5 mL) and quenched with water. The organic layer was then washed with dil.HCI (1N), dil.NaHCO$_3$, water, and finally brine. The organic layer was separated, dried over Na$_2$SO$_4$, and concentrated under reduced pressure to yield the crude product. The crude product thus obtained was purified using PTLC (silica gel, 500 m, ethylacetate:hexanes, 1:3) to yield compounds 8 (80–90%).

4-Deacetyl-4-(S-methylxanthyl)-2'-tert-Butyl-dimethylsilyl-7-triethylsilylpaclitaxel 1,2-Carbonate (8a)

4-Deacetyl-2'-tert-butyldimethylsilyl-7-triethylsilylpaclitaxel 1,2-carbonate (7) (80.0 mg , 0.0825 mmol) was dissolved in freshly distilled dry THF (0.5 mL). Sodium hydride (6.0 mg, 0.250 mmol) was added at room temperature, followed by carbon disulfide (0.2 mL, excess). After stirring for 5 minutes at room temperature, methyl iodide (0.1 mL, excess) was added and stirred at room temperature. The reaction was completed in 1 hour. The mixture was diluted with EtOAc and washed with dil HCl, water and brine. The organic layer was separated, dried over sodium sulfate and evaporated. The crude product thus obtained was further purified with preparative TLC (1000μ, silicagel, 1:3 ethylacetate: hexanes) to yield amorphous solid 8a (77.4 mg, 90%). FABMS m/z (rel int.) [M+H]$^+$ 1052 (7), 1022 (15), 514 (4), 400 (20), 354 (75), 105 (100); HRFABMS m/z [M+H]$^+$ 1052.4120 (C$_{53}$H$_{73}$NO$_{13}$S$_2$Si$_2$ requires 1052.4062).

Reaction of 2'-tert-Butyldimethysilyl-7-triethysilyl-4-acylpactaxel 1,2-Carbonate Derivatives (8) With LiOH/THF, Water A mixture of the title compound 8 (60.0 mg, mmol) and LiOH (20.0 mmg, mmol) in wet THF (0.5 mL, 2 or 3 drops of water) was stirred at room temerature for 2–3 hours. Monitoring the reaction by TLC indicated the formation of a low Rf (0.3) spot. The mixture was then diluted with EtOAc and water. The organic layer was separated, washed with brine, and evaporated to yield crude product. Purification of the crude product by preparative TLC afforded the starting compound (15.5 mg, 25%) as a non polar band and the 2-debenzoyl derivative 9 as a polar band (38.0 mg, 70%).

Reaction of 4-(S-Methylxanthyl)-2'-tert-Butyldimethyl Silyl-7-triethylsilylpaclitaxel 1,2.Carbonate (8a) With LiOH/THF, Water A mixture of the title compound 8a (60.0 mg, mmol) and LiOH (20.0 mmg, mmol) in wet THF (0.5 mL, 2 or 3 drops of water) was stirred at room temperature for 2–3 hours. Monitoring the reaction by TLC indicated the formation of a low Rf (0.3) spot. The mixture was then diluted with EtOAc and water. The organic layer was separated, washed with brine, and evaporated to yield crude product. Purification of the crude product by preparative TLC afforded the 2-debenzoyl-4-(S-methylxanthyl) derivative 9a as a polar band (52.4 mg, 89%).

General Procedure for Aroylation of 2-Debenzoyl-4-deacetyl-4-acylpaclitaxel Analogs (5 and 5a)

A substituted benzoic acid (0.2 mmol) was taken in dry toluene (0.2 mL). To this solution DCC (20.6 mg, 0.1 mmol) and 4-pyrrolidino pyridine (1.0 mg, 0.006 mmol) were added. The mixture was stirred at room temperature for 5 minutes. To this mixture a 2-debenzoyl-4-deacetyl-4-acyl-2'-tert-butyl-7-triethylsilylpaclitaxel analog (9) (10.0 mg, 0.01 mmol) was added. The reaction mixture was stirred either at room temperature or heated on an oil bath at 60° until the starting compound was consumed (TLC analysis, generally 4–16 hours). The reaction mixture was diluted with EtOAc (10 mL) and filtered through a pad of silica gel and celite. This pad was further washed with EtOAc (10 mL). The EtOAc filtrate was concentrated on a rotary evaporator to give crude product. Further purification using preparative TLC (silica gel; 500 m, hexane:EtOAc; 2:1) gave 2-substituted benzoyl-2'-tert-butyl-7-triethylsilypaclitaxel analogs 5 and 5a respectively (60–90% yield).

General Procedure for Deprotection of Silyl Groups of Derivatives (5) by Methanol/HCL 2-Debenzoyl-2-aroyl-4-deacetyl-4-acyl-2'-tert-butyl-7-triethylsilyl paclitaxel 5 (0.005 mmol) was dissolved in freshly prepared methanolic HCl (5%, v/v) solution. The mixture was kept stirring at room temperature for 45–60 minutes. The mixture was diluted with EtOAc (10 mL) and washed with dil. $NaHCO_3$ solution, water and brine. The organic layer was dried over sodium sulfate and concentrated to give crude product. Further purification was carried out using preparative TLC to give homogenous product 6 (70–90%).

General Procedure for Deprotection of Silyl Groups of Derivatives (5a) by HF/Pyridine To a solution of 2-debenzoyl-2-aroyl-4-deacetyl-4-(S-methylxanthyl) derivatives 5a (0.005 mmol) in dry THF (0.5 mL) was added HF/pyridine at room temperature. The exothermic reaction mixture was then stirred at room temperature for 2 hours. The reaction mixture was diluted with EtOAc and washed with dil. $NaHCO_3$, dil. HCl and finally brine. The organic layer was separated, dried over $Na_2SO_4$, and evaporated to yield crude material. Further purification by PTLC afforded 2-debenzoyl-2-aroyl-4-deacetyl-4-(S-methylxanthyl) paclitaxel analogs 6a.

2'O-tert-Butyldimethylsiyl-7-O-triethysilyl-2-debenzoyl-4-deacetyl-4-(methoxycarbonyl)-paclitaxel To a solution of 2'-O-tert-Butyldimethylsilyl-7-O-triethylsilyl-2-debenzoyl-4-deacetyl-4-(methoxycarbonyl)-paclitaxel 1,2-carbonate (8b) (50 mg, 0.49 mmol) in THF (1 mL) and water (0.1 mL), LiOH (20 mg, 0.64 mmol) was added and stirred at room temperature for 1.5 hours. The mixture was taken up in EtOAc (10 mL), washed with water and brine, and dried over sodium sulfate. The residue obtained after concentration was purified by PTLC (silica gel, 1000 $\mu$M, EtOAc:hexane, 2:3) to furnish 2'-O-tert-butyldimethylsilyl-7-O-triethylsilyl-2-debenzoyl-4-deacetyl-4-(methoxycarbonyl)-paclitaxel (9b) (20 mg, 59% yield based on the recovery of 15 mg unreacted starting compound) and 2'-O-tert-butyldimethylsilyl-7-O-triethylsilyl-2-debenzoyl-4-deacetyl-paclitaxel (6 mg). $^1$H NMR: $\delta$, −0.27 (s, 3H), −0.06 (s, 3H), 0.54–0.60 (m, 6H), 0.79 (s, 9H), 0.89–0.96 (m, 9H), 1.03 (s, 3H), 1.09 (s, 3H), 1.22–1.27 (m, 1H), 1.85 (s, 3H), 1.86–1.95 (m, 1H), 2.04 (s, 3H), 2.08–2.14 (m, 1H), 2.12 (s, 3H), 2.25–2.29 (m, 1H), 2.45–2.53 (m, 1H), 3.24 (d, J=4.28 Hz, 1H), 3.30 (s, 1H), 3.52 (d, J=6.86 Hz, 1H), 3.86 (s, 3H), 3.92–3.95 (m, 1H), 4.37–4.41 (m, 1H), 4.52 (d, J=1.37 Hz, 1H), 4.65 (d, J=9.46 Hz, 1H), 4.70 (d, J=9.61 Hz, 1H), 4.98 (d, J=7.78 Hz, 1H), 5.70 (d, J=9.31 Hz, 1H), 6.18 (dd, J=8.7, 8.24 Hz, 1H), 6.35 (s, 1H), 7.09 (d, J=9.46 Hz, 1H), 7.29–7.52 (m, 8H), 7.72 (d, J=7.17 Hz, 2H); $^{13}$C NMR: $\delta$, −5.78, −5.25, 5.23, 6.71, 10.32, 14.21, 18.14, 20.81, 21.12, 25.42, 25.48, 26.26, 35.41, 37.24, 42.92, 46.73, 55.41, 55.87, 58.09, 71.46, 72.05, 73.75, 74.96, 75.14, 77.78, 78.03, 83.66, 84.26, 126.22, 126.62, 126.91, 126.99, 127.93, 128.49, 128.59, 128.83, 131.86, 134.17, 143.20, 138.41, 139.72, 152.91, 167.56, 169.24, 171.51, 202.27; HRFABMS: m/z [M+H]$^+$ 994.4822 ($C_{52}H_{76}NO_{14}Si_2$ requires 994.4802).

2'-O-tert-Butyldimethysilyl-7-O-triethysilyl-2-debenzoyl-2-(3-azido benzoyl)-4-deacetyl-4-(methoxcarbonyl)-paclitaxel (5b)

To a mixture of the 2'-O-tert-butyldimethylsilyl-7-O-triethylsilyl-2-debenzoyl-4-deacetyl-4-(methoxycarbonyl)-paclitaxel (10 mg, 0.01 mmol), m-azidobenzoic acid (16 mg, 0.09 mmol) and pyrrolidinopyridine (1.0 mg) was added toluene (0.8 mL) and the reaction mixture was stirred at room temperature for 24 hours and purified by PTLC (silica gel, 1000 $\mu$M, EtOAc-hexane, 2:3) to yield 2'-O-tert-butyldimethylsilyl-7-O-triethylsilyl-2-debenzoyl-2-(3-azidobenzoyl)-4-deacetyl-4-(methoxycarbonyl)-paclitaxel (9.0 mg, 79%). $^1$H NMR: $\delta$, −0.30 (s, 3H), −0.03 (s, 3H), 0.54–0.61 (m, 6H), 0.78 (s, 9H), 0.91–0.94 (m, 9H), 1.15 (s, 3H), 1.22 (s, 3H), 1.66–1.68 (m, 1H), 1.70 (s, 3H), 1.81 (s, 3H), 1.89–1.96 (m, 1H), 2.06 (s, 3H), 2.12–2.17 (m, 1H), 2.17 (s, 3H), 2.38–2.44 (m, 1H), 2.52–2.55 (m, 1H), 3.94 (d, J=6.87 Hz, 1H), 4.03 (s, 3H), 4.21 (d, J=8.85 Hz, 1H), 4.37 (d, J 8.24 Hz, 1H), 4.43–4.48 (dd, J=6.87, 6.56 Hz, 1H), 4.67 (d, J=1.68 Hz, 1H), 5.10 (d, J=7.63 Hz, 1H), 5.71 (d, J=7.02 Hz, 1H), 5.77 (d, J=9.76 Hz, 1H), 6.20–6.24 (dd, J=7.94, 9.16 Hz, 1H), 6.46 (s, 1H), 7.09 (d, J=9.31 Hz, 1H), 7.21–7.52 (m, 10H), 7.73–7.78 (d, J=7.17 Hz, 3H), 7.92 (d, J=7.78 Hz, 1H). $^{13}$C NMR: $\delta$, −5.21, −5.25, 6.73, 10.09, 14.40, 18.11, 20.84, 21.09, 25.48, 26.50, 35.58, 32.12, 43.23, 46.71, 55.44, 56.47, 58.25, 70.86, 72.03, 75.01, 75.10, 75.25, 78.53, 83.17, 83.97, 120.45, 124.00, 126.49, 126.56, 126.93, 127.79, 128.57, 128.73, 130.25, 131.70, 133.65, 134.30, 140.43, 140.89, 152.56, 166.10, 166.91, 169.25, 171.51, 201.47. HRFABMS:m/z [M+H]$^+$ 1139.5061 (calcd for $C_{59}H_{79}N_4O_{15}Si_2$, 1139.5080).

2-Debenzoyl-2-(3-azidobenzoil)-4-deacetyl-4-(methoxy-carbonyl)-paclitaxel (6b)

To a solution of 2'-O-tert-butyldimethylsilyl-7-O-triethylsilyl-2-debenzoyl-2-(3-azido benzoyl)-4-deacetyl-4-(methoxycarbonyl)-paclitaxel (8.0 mg, 0.007 mmol) in dry THF was added HF-pyridine (0.2 mL) in a Teflon vial. The reaction mixture was stirred at room temperature for 2 hours. The mixture was then diluted with EtOAc (10 mL) and washed thoroughly with dilute sodium bicarbonate, dilute HCl, water and finally brine. The organic layer was dried over sodium sulfate and evaporated to yield crude product, which was purified by PTLC (500 μM, 55% EtOAc/Hexane) to give 2-debenzoyl-2-(3-azidobenzoyl)-4-deacetyl-4-(methoxycarbonyl)-paclitaxel (6b, 6.3 mg, 98%) $^1$H NMR: δ, 1.14 (s, 3H), 1.24 (s, 3H), 1.67 (s, 3H), 1.85 (s, 3H), 1.88 (s, 1H), 1.89–1.93 (m, 1H), 2.24 (s, 3H), 2.35–2.57 (m, 4H), 3.57 (d, J=4.89 Hz, 1H), 3.77 (s, 3H), 3.84 (d, J=6.86 Hz, 1H), 4.20 (d, J=8.39 Hz, 1H), 4.34–4.41 (m, 2H), 4.47–4.79 (m, 1H), 4.99 (d, J=9.00 Hz, 1H), 5.69 (d, J=7.17 Hz, 1H), 5.80 (d, J=8.85 Hz, 1H), 6.18–6.22 (dd, J=7.78, 9.00 Hz, 1H), 6.27 (s, 1H), 6.87 (d, J=9.01 Hz, 1H), 7.24–7.51 (m, 10H), 7.57 (d, J=7.63 Hz, 2H), 7.70 (d, J=7.02 Hz, 2H), 7.82–7.83 (m, 1H), 7.94 (d, J=7.79 Hz, 1H. HRFABMS: m/z [M+H]$^+$ 911.3343 ($C_{47}H_{51}N_4O_{15}$ requires 911.3350).

2'-tert-Butyldimethysilyl-7-O-triethysilyl-2-debenzoyl-2-(3,3-dimethyl-acryloyl)-4-deacetyl-4-(methoxycarbonyl)-paclitaxel (5c)

A mixture of the 2'-O-tert-butyldimethylsilyl-7-O-triethylsilyl-2-debenzoyl-4-deacetyl-4-(methoxycarbonyl)-paclitaxel (9b, 10 mg, 0.01 mmol), 3,3-dimethylacrylic acid (10 mg, 0.1 mmol) and pyrrolidinopyridine (1.0 mg) in toluene (0.8 mL) was stirred at room temperature for 24 hours and purified by PTLC (silica gel, 1000 μM, EtOAc hexane, 3:7) to yield 2'-O-tert-butyldimethylsilyl-7-O-triethylsilyl-2-debenzoyl-2-(3,3-dimethylacryloyl)-4-deacetyl-4-(methoxycarbonyl)-paclitaxel (5c, 7.0 mg, 95% based on the recovery of 2 mg unreacted starting compound). $^1$H NMR: δ, −0.35 (s, 3H), −0.04 (s, 3H), 0.52–0.62 (m, 6H), 0.78 (s, 9H), 0.87–0.93 (m, 9H), 1.14 (s, 3H), 1.18 (s, 3H), 1.25 (s, 3H), 1.67 (s, 3H), 1.89 (s, 3H), 1.97 (d, J=0.92 Hz, 3H), 2.02 (d, J=0.92 Hz, 3H), 1.91–2.22 (m, 3H), 2.16 (s, 3H), 2.19 (s, 3H), 2.52–2.55 (m, 1H), 3.78 (d, J=6.72 Hz, 1H), 4.00 (s, 3H), 4.22 (d, J=8.85 Hz, 1H), 4.39–4.43 (dd, J=6.86, 6.72 Hz, 1H), 4.52 (d, J=8.39 Hz, 1H), 4.65 (d, J=1.68 Hz, 1H), 5.03 (d, J=7.62 Hz, 1H), 5.48 (d, J=6.72 Hz, 1H), 5.67–5.70 (m, 2H), 6.20–6.25 (dd, J=9.46, 9.76 Hz, 1H), 6.43 (s, 1H), 7.13 (d, J=8.70 Hz, 1H), 7.27–7.55 (m, 8H), 7.78 (d, J=6.92 Hz, 1H). HRFABMS: m/z [M+H]$^+$ 1076.5206 (calcd for $C_{57}H_{82}NO_{15}Si_2$, 1076.5223).

2-Debenzoyl-2-(3,3-dimethyl-acryloyl)-4-deacetyl-4-(methyl Carbonate)-paclitaxel (6c)

To a solution of 2'-O-tert-butyldimethylsilyl-7-O-triethylsilyl-2-debenzoyl-2-(3,3-dimethyl-acryloyl)-4-deacetyl-4-(methoxycarbonyl)-paclitaxel (6.0 mg, 0.005 mmol) in dry THF (1 mL) was added HF-pyridine (0.2 mL) in a Teflon vial. The reaction mixture was stirred at room temperature for 2 hours. After usual workup the residue obtained was purified by PTLC (500 μM, 55% EtOAc/hexane) to give 2-debenzoyl-2-(3,3-dimethyl acryloyl)-4-deacetyl4-(methoxycarbonyl)-paclitaxel (6c, 3.9 mg, 98%). $^1$H NMR: δ, 1.10 (s, 3H), 1.21 (s, 3H), 1.63 (s, 3H), 1.79 (d, J=1.22 Hz, 3H), 1.83 (s, 3H), 1.86–1.89 (m, 1H), 1.95 (d, J=1.07 Hz, 3H), 2.19 (s, 3H), 2.23 (s, 3H), 2.26–2.34 (m, 2H), 2.44 (d, J=4.27 Hz, 1H), 2.50–2.58 (m, 1H), 3.58 (d, J=4.27 Hz, 1H), 3.70 (d, J=6.71 Hz, 1H), 3.78 (s, 3H), 4.20 (d, J=8.24 Hz, 1H), 4.34 (m, 1H), 4.51 (d, J=8.85 Hz, 1H), 4.74–4.76 (dd, J=2.29, 2.13 Hz, 1H), 4.99 (d, J=7.79 Hz, 1H), 5.46 (d, J=6.71 Hz, 1H), 5.71 (s, 1H), 5.78 (d, J=8.85 Hz, 1H), 6.15 (m, 1H), 6.23 (s, 1H), 6.95 (d, J=9.77 Hz, 1H), 7.30–7.55 (m, 8H), 7.77 (d, J=7.02 Hz, 1H). HRFABMS: m/z [M+H]$^+$ 848.3501 (calcd for $C_{45}H_{54}NO_{15}$, 848.3493).

2'-O-tert-Butyldimethysilyl-7-O-Triethysilyl-2-debenzoyl-4-deacetyl-4-(tert-butoxy-carbonyl)-paclitaxel 1,2-Carbonate (8c)

To a stirred solution of 2'-O-tert-butyldimethylsilyl-7-O-triethylsilyl-2-debenzoyl-4-deacetyl-paclitaxel 1,2-carbonate (80 mg, 0.083 mmol), DMAP (15 mg) in $CH_2Cl_2$ di-tert-butyldicarbonate (180 mg, 0.83 mmol) was added and the mixture was stirred at room temperature for 6 hours. It was diluted with $CH_2Cl_2$ (20 mL) and washed thoroughly with water and brine. The organic layer was dried over sodium sulfate and evaporated to yield crude product, which was purified by PTLC (1000 μM, EtOAc/hexane, 3:7) to give 2'-O-tert-butyldimethylsilyl-7-O-triethylsilyl-2-debenzoyl-4-deacetyl-4-(tert-butoxycarbonyl)-paclitaxel 1,2-carbonate (8c, 82 mg, 93%). $^1$H NMR: δ, −0.41 (s, 3H), −0.03 (s, 3H), 0.55–0.60 (m, 6H), 0.79 (s, 9H), 0.90 (t, J=8.24 Hz, 9H), 1.22 (s, 3H), 1.31 (s, 3H), 1.53 (s, 9H), 1.76 (s, 3H), 1.81–2.00 (m, 1H), 2.03 (s, 3H), 2.15 (s, 3H), 2.35–2.41 (m, 1H), 2.50–2.56 (dd, J=9.31, 9.46 Hz, 1H), 2.62–2.69 (m, 1H), 3.54 (d, J=5.80 Hz, 1H), 4.37–4.41 (dd, J=7.48, 7.17 Hz, 1H), 4.50–4.56 (dd, J=9.00, 5.96 Hz, 2H), 4.75–4.77 (m, 2H), 5.08 (d, J=8.55 Hz, 1H), 5.89 (d, J=9.31 Hz, 1H), 6.21–6.25 (dd, J=8.4, 8.24 Hz, 1H), 6.46 (s, 1H), 7.01 (d, J=9.31 Hz, 1H), 7.23–7.55 (m, 8H), 7.81 (d, J=7.02 Hz, 1H). $^{13}$C NMR: δ, −5.89, −5.16, 5.19, 6.71, 10.16, 15.30, 17.98, 20.59, 20.72, 25.45, 25.55, 28.70, 32.78, 38.10, 41.39, 43.51, 55.29, 60.08, 69.19, 71.71, 75.18, 75.83, 80.90, 81.45, 83.81, 86.78. 89.97, 126.82, 127.05, 127.47, 128.24, 128.73, 131.17, 131.66, 134.40, 138.22, 143.76, 151.18, 152.40, 166.83, 169.02, 171.70, 201.90; HRFABMS: m/z [M+H]$^+$ 1062.5079 (calcd for $C_{56}H_{80}NO_{15}Si_2$, 1062.5066).

2'-O-tert-Butyldimethysilyl-7-O-triethysilyl-4-deacetyl-4-(tert-butoxy-carbonyl)-paclitaxel (5d) and 2'-O-tert-Butyldimethylsily-7-O-triethylsilyl-10,4-di-deacetyl-4-(tert-butoxycarbonyl)-paclitaxel (5e)

To a dry THF (1.5 mL) solution of 2'-O-tert-butyldimethylsilyl-7-O-triethylsilyl-2-debenzoyl-4-deacetyl-4-(tert-butoxy-carbonyl)-paclitaxel 1,2-carbonate (15 mg, 0.014 mmol) was added under argon a hexane solution of phenyllithium (1.6 M, 78 μL, 0.14 mmol). The solution was stirred at −78° C. for 20 min and 0° C. for 5 min. Then it was poured on a mixture of EtOAc (10 mL) and dilute HCl (0.1 N, 2 mL). After standard workup, the residue was purified on PTLC (500 μM, EtOAc/hexane, 3:7) to give two products: 2'-O-tert-butyldimethylsilyl-7-O-triethylsilyl-4-deacetyl-4-(tert-butoxycarbonyl)-paclitaxel (5d, 6.1 mg, 38%) and 2'-O-tert-butyldimethylsilyl-7-O-triethylsilyl-10,4-di-deacetyl-4-(tert-butoxy carbonyl)-paclitaxel (5e, 6.8 mg, 44%). Compound 5d: $^1$H NMR: δ, −0.30 (s, 3H), −0.04 (s, 3H), 0.52–0.58 (m, 6H), 0.88 (s, 9H), 0.89–0.98 (m, 9H), 1.22 (s, 3H), 1.24 (s, 3H), 1.59 (s, 9H), 1.61 (s, 3H), 1.72 (s, 3H), 1.82–1.92 (m, 2H), 2.23 (s, 3H), 2.51–2.53 (m, 2H), 3.84 (d, J=6.40 Hz, 1H), 4.21 (d, J=8.55 Hz, 1H), 4.35–4.42 (m, 2H), 4.68 (m, 1H), 4.98 (d, J=7.02 Hz, 1H), 5.73–5.79 (m, 2H), 6.12 (m, 1H), 6.41 (s, 1H), 7.13 (d, J=9.00 Hz, 1H), 7.23–7.58 (m, 1H), 7.78 (d, J=7.02 Hz, 2H), 8.06 (d, J=7.02 Hz, 1H). Compound 5e: $^1$H NMR: δ, −0.32 (s, 3H), −0.04 (s, 3H), 0.55–0.61 (m, 6H), 0.87 (s, 9H), 0.88–0.97 (m, 9H), 1.08 (s, 3H), 1.12 (s, 3H), 1.57 (s, 9H), 1.71 (s, 3H), 1.70–1.92 (m, 2H), 2.21 (s, 3H), 2.53–2.58 (m, 2H), 3.90 (d, J=6.72 Hz, 1H), 4.26 (d, J=9.40 Hz, 1H), 4.32–4.45 (m, 2H), 4.64 (s, 1H), 4.98 (d, J=7.48 Hz, 1H), 4.76–4.80 (m, 2H), 6.12 (m, 1H), 7.12 (d, J=9.00 Hz, 1H), 7.28–7.61 (m, 11H), 7.78 (d, J=7.02 Hz, 2H), 8.04 (d, J=7.02 Hz, 2H).

4-Deacetyl-4-(tert-butoxycarbonyl)-paclitaxel (6d)

To a solution of 2'-O-tert-butyldimethylsilyl-7-O-triethylsilyl-4-deacetyl-4-(tert-butoxycarbonyl)-paclitaxel (5d, 6.1 mg, 0.005 mmol) in dry THF (1 mL) was added HF-Pyridine (0.4 mL) in a Teflon vial. The reaction mixture was stirred at room temperature for 2 hours. After usual workup, the residue obtained was purified by PTLC (500 μM, 55% EtOAc/hexane) to give 4-deacetyl-4-(tert-butoxycarbonyl)-paclitaxel (4.3 mg, 89%). $^1$H NMR: δ, 1.14 (s, 3H), 1.23 (s, 3H), 1.51 (s, 9H), 1.61 (s, 3H), 1.73 (s, 3H), 1.74 (s, 1H), 1.84–1.90 (m, 2H), 2.24 (s, 3H), 2.39–2.43 (m, 1H), 2.48 (d, J=3.97 Hz, 1H), 2.50–2.54 (m, 1H), 3.73 (s, 1H), 3.81 (d, J=6.41 Hz, 1H), 3.92 (d, J=3.82 Hz, 1H), 4.21 (d, J=8.55 Hz, 1H), 4.33 (m, 1H), 4.40 (d, J=8.55 Hz, 1H), 4.80 (m, 1H), 4.98 (d, J=6.71 Hz, 1H), 5.70 (d, J=7.13 Hz, 1H), 5.83 (d, J=6.71 Hz, 1H), 6.11–6.14 (m, 1H), 6.24 (s, 1H), 7.15–7.62 (m, 11H), 7.79 (d, J=7.32 Hz, 2H), 8.04 (d, J=7.17 Hz, 2H). HRFABMS: m/z 934.3648 [M+Na]$^+$ (calcd for $C_{50}DH_{57}NO_{15}Na$, 934.3625).

10,4-di-Deacetyl-4-(tert-Butoxycarbonyl)-paclitaxel (6e)

To a solution of 2'-O-tert-butyldimethylsilyl-7-O-triethylsilyl-4,10-di-deacetyl-4-(tert-butoxycarbonyl)-paclitaxel (5e, 6.1 mg, 0.005 mmol) in dry THF (1 mL) was added HF-pyridine (0.4 mL) in a Teflon vial. The reaction mixture was stiffed at room temperature for 2 hours. After usual workup, the residue obtained was purified by PTLC (500 μM, 55% EtOAc/hexane) to give 10,4-dideacetyl-4-(tert-butoxycarbonyl)-paclitaxel (4.1 mg, 85%). 1H NMR: δ1.11 (s, 3H), 1.20 (s, 3H), 1.52 (s, 9H), 1.71 (s, 3H), 1.68–1.89 (m, 2H), 2.39 (s, 3H), 2.39 (d, J=9.00 Hz, 2H), 2.52–2.59 (m, 1H), 3.90 (d, J=3.35 Hz, 1H), 3.92 (d, J=6.72 Hz, 1H), 4.13 (m, 1H), 4.17 (d, J=1.68 Hz, 1H), 4.26 (d, J=9.46 Hz, 1H), 4.78–4.80 (dd, J=2.59, 3.51 Hz, 1H), 4.96 (d, J=7.78 Hz, 1H), 5.17 (d, J=1.83 Hz, 1H), 5.71 (d, J=6.71 Hz, 1H), 5.83 (d, J=9.00 Hz, 1H), 6.06–6.09 (dd, J=7.02, 8.70 Hz, 1H), 7.25–7.51 (m, 10H), 7.60 (dd, J=7.47, 7.78 Hz, 1H), 7.79 (d, J=7.02 Hz, 2H), 8.03 (d, J=7.02 Hz, 2H). HRFABMS: m/z [M+H]$^+$ 870.3698 (calcd for $C_{48}H_{56}NO_{14}$, 870.3700).

2'-O-tert-Butyldimethysilyl-7-O-triethysilyl-2-debenzoyl-2-(m-methoxy-benzoyl)-4-deacetyl-4-(tert-butoxycarbonyl)-paclitaxel (5f)

To a dry THF (1.5 mL) solution of 2'-O-tert-butyldimethylsilyl-7-O-triethylsilyl-2-debenzoyl-1,2-carbonate-4-deacetyl-4-(tert-butoxy carbonyl)-paclitaxel (15 mg, 0.014 mmol) was added under argon a THF solution of m-methoxyphenyllithium [prepared from 1.6 M n-butyllithium (90, μL, 0.14 mmol) and m-bromoanisole (17 μL, 0.14 mmol)]. The solution was stirred at −78° C. for 20 min and 0° C. for 5 min. After standard workup, the residue was purified on PTLC (500 μM, EtOAc/hexane, 3:7) to give two products 2'-O-tert-butyldimethylsilyl-7-O-triethylsilyl-2-debenzoyl-2-(m-methoxybenzoyl)-4-deacetyl-4-(tert-butoxycarbonyl)-paclitaxel (8.0 mg, 90%, based on the recovery of 7 mg unreacted staring compound). $^1$H NMR: δ, −0.30 (s, 3H), −0.03 (s, 3H), 0.51–0.59 (m, 6H), 0.82 (s, 9H), 0.95–0.99 (m, 9H), 1.22 (s, 3H), 1.59 (s, 9H), 1.71 (s, 3H), 1.91–2.04 (m, 1H), 2.03 (s, 3H), 2.19–2.24 (m, 1H), 2.21 (s, 3H), 2.48–2.52 (m, 2H), 3.81 (d, J=7.18 Hz, 1H), 3.93 (s, 3H), 4.22 (d, J=9.16 Hz, 1H), 4.42–4.56 (m, 2H), 4.64 (s, 1H), 4.98 (d, J=7.48 Hz, 1H), 5.72–5.78 (m, 2H), 6.16 (m, 1H), 6.44 (s, 1H), 7.11–7.52 (m, 10H), 7.71–7.78 (m, 4H).

2-Debenzoyl-2-(m-methoxybenzoyl)-4-deacetyl-4-(tert-butoxy carbonyl)-paclitaxel (6f)

To a solution of 2'-O-tert-butyldimethylsilyl-7-O-triethylsilyl-2-debenzoyl-2-(m-methoxybenzoyl)-4-deacetyl-4-(tert-butoxycarbonyl)-paclitaxel (5f, 8.0 mg, 0.006 mmol) in dry THF (1 mL) was added HF-pyridine (0.2 mL) in a Teflon vial. The reaction mixture was stirred at room temperature for 1 hour. After usual workup, the residue obtained was purified by PTLC (500 μM, 55% EtOAc/hexane) to give 2-debenzoyl-2-(m-methoxybenzoyl)-4-deacetyl-4-(tert-butoxycarbonyl)-paclitaxel (6f, 4.1 mg, 64%). $^1$H NMR: δ, 1.14 (s, 3H), 1.26 (s, 3H), 1.47 (s, 9H), 1.68 (s, 3H), 1.76 (s, 3H), 1.76 (s, 3H), 1.83 (s, 1H), 1.86–1.94 (m, 1H), 2.24 (s, 3H), 2.36–2.44 (m, 2H), 2.48 (d J=3.97 Hz, 2H), 2.53–2.58 (m, 1H), 3.78 (d, J=7.17 Hz, 1H), 3.80 (d, J=3.81 Hz, 1H), 3.87 (s, 3H), 4.21 (d, J=9.16 Hz, 1H), 4.38 (m, 1H), 4.41 (d, J=8.24 Hz, 1H), 4.80–4.81 (dd, J=2.29, 2.44 Hz, 1H), 4.96 (d, J=7.48 Hz, 1H), 5.68 (d, J=7.02 Hz, 1H), 5.82 (d, J=11.14 Hz, 1H), 6.16 (m, 1H), 6.24 (s, 1H), 7.05 (d, J=9.00 Hz, 1H), 7.12–7.15 (m, 1H), 7.29–7.53 (m, 9H), 7.64 (d, J=7.02 Hz, 2H), 7.74 (d, J=7.02 Hz, 2H). HRFABMS: m/z [M+H]$^+$ 942.3912 (calcd for $C_{51}H_{60}NO_{16}$, 942.3912).

REFERENCES (1) Chaudhary, A. G.; Gharpure, M. M.; Rimoldi, J. M.; Chordia, M. D.; Gunatilaka, A. A. L.; Kingston, D. G. I.; Grover, S.; Lin, C. M.; Hamel, E., Unexpectedly Facile Hydrolysis of the 2-Benzoate Group of PACLITAXEL and Synthesis of Analogs with Increased Activities, *J. Am. Chem. Soc.*, 1994, 116, 4097–4098.

(2) Georg, G. I.; Harriman, G. C. B.; Ali, S. M.; Datta, A.; Hepperle, M.; Himes, R. H., Synthesis of 2-0-Heteroaroyl Taxanes: Evaluation of Microtubule Assembly Promotion and Cytotoxicity, *Bioorg. & Med. Chem. Lett.*, 1995, 5, 115–118.

(3) Grover, S.; Rimoldi, J. M.; Molinero, A. A.; Chaudhary, A. G.; Kingston, D. G. I.; Hamel, E., Differential Effects of Paclitaxel (Taxol) Analogs Modified at Positions C-2, C-7, and C-3' on Tubulin Polymerization and Polymer Stabilization: Identification of a Hyperactive Paclitaxel Derivative, Biochemistry, 1995, 34, 3927–3934.

(4) Nicolaou, K. C.; Renaud, J.; Nantermet, P. G.; Couladouros, E. A.; Guy, R. K.; Wrasidlo, W. Chemical Synthesis and Biological Evaluation of C-2 Taxoids, *J. Am. Chem. Soc.*, 1995, 117, 2409–2420.

(5) Georg, G. I.; Ali, S. M.; Boge, T. C.; Datta, A.; Falborg, L.; Park, H.; Mejillano, M.; Himes, R. H., Synthesis of Biologically Active 2-Benzoyl Paclitaxel Analogs, *Bioorg. & Med. Chem. Lett.*, 1995, 5, 259–264.

(6) Georg, G. I.; Boge, T. C.; Park, H.; Himes, R. H., Paclitaxel and Docetaxel Photoaffinity Labels, *Bioorg. & Med. Chem. Lett.*, 1995, 5, 615–620.

(7) Nicolaou, K. C.; Couladouros, E. A.; Nantermet, P. G.; R$_e$naud, J.; Guy, R. K.; Wrasidlo, W., Synthesis of C-2 Taxol Analogs, *Angew. Chem. Int. Ed. Engl.*, 1994, 33, 1581–1583.

(8) Pulicani, J.-P.; Bezard, D.; Bourzat, J.-D.; Bouchard, H.; Zucco, M.; Deprez, D.; Commercon, A., Direct Access to 2-Debenzoyl Taxoids by Electrochemistry, Synthesis of 2-Modified Docetaxel Analogs, *Tetrahedron Lett.*, 1994, 35, 9717–9720.

(9) Ojimd, I.; Duclos, O.; Zucco, M.; Lavelle, F., Synthesis and Structure Activity Relationships of New Antitumor Taxoids, Effects of Cyclohexyl Substitution at the C-3'and/or C-2 of Taxotere (Docetaxel), *J. Med. Chem.*, 1994, 37, 2602–2608.

(10) Boge, T. C.; Himes, R. H.; Vander Velde, D. G.; Georg, G. I., The Effect of the Aromatic Rings of Taxol on Biological Activity and Solution Conformation: Synthesis and Evaluation of Saturated Taxol and Taxotere Analogs, *J. Med. Chem.*, 1994, 37, 3337–3343.

(11) Neidigh, K. A.; Gharpure, M. M.; Rimoldi, J. M.; Kingston, D. G. I.; Jiang, Y. Q.; Hamel, E., Synthesis and Biological Evaluation of 4-Deacetylpaclitaxel, *Tetrahedron Lett.*, 1994, 35, 6839–6842.

(12) Datta, A.; Jayasinghe, L. R.; Georg, G. I, 4-Deacetyltaxol and 10-Acetyl-4-deacetyltaxotere: Synthesis and Biological Evaluation, *J. Med. Chem.*, 1994, 37, 4258–4260.

(13) Georg, G. I.; Ali, S. M.; Boge, T. C.; Datta, A.; Falborg, L.; Himes, R. H. Selective C-2 and C-4 Deacylation and Acylation of Taxol: The First Synthesis of a C-4 Substituted Taxol Analog, *Tetrahedron Lett.*, 1994, 35, 8931–8934.

(14) Chen, S.-H.; Kadow, J. F.; Farina, V.; Fairchild, C. R.; Johnston, K. A. First Syntheses of Novel Paclitaxel (Taxol) Analogs Modified at the C-4-Position, *J. Org. Chem.*, 1994, 59, 6156–6158.

(15) Chordia, M. D.; Chaudhary, A. G.; Kingston, D. G. I.; Jiang, Y. Q.; Hamel, E., Synthesis and Biological Evaluation of 4-Deacetoxypaclitaxel, *Tetrahedron Lett.*, 1994, 35, 6843–6846.

(16) Chen, S.-H.; Kant, J.; Mamber, S.W.; Roth, G.P.; Wei, J.-M.; Marshall, D.; Vyas, D. M.; Farina, V., Taxol Structure-Activity Relationships: Synthesis and Biological Evaluation of Taxol Analogs Modified at C-7, *Bioorg. Med. Chem. Lett.*, 1994, 4, 2223–2228.

(17) Magri, N. F.; Kingston, D. G. I., Modified Taxols. 2. Oxidation Products of Taxol, *J. Org. Chem.*, 1986, 51, 797–802.

(18) Mellado, W.; Magri, N. F.; Kingston, D. G. I.; Garcia-Arenas, R.; Orr, G. A.; Horwitz, S. B., Preparation and Biological Activity of Taxol Acetates, *Biochem. Biophys. Res. Commun.*, 1984, 124, 329–335.

(19) Deutsch, H. M.; Glinski, J. A.; Hernandez, M.; Haugwitz, R. D.; Narayanan, V. L.; Suffness, M.; Zalkow, L. H., Synthesis of Congeners and Prodrugs. 3. Water-Soluble Prodrugs of Taxol with Potent Antitumor Activity, *J. Med. Chem.*, 1989, 32, 788–792.

(20) Kant, J.; O'Keeffe, W. S.; Chen, S.-H.; Farina, V.; Fairchild, C.; Johnston, K.; Kadow, J. F.; Long, B. H.; Vyas, D., A Chemoselective Approach to Functionalize the C-10 Position of 10-Deacetylbaccatin III. Synthesis and Biological Properties of Novel C-10 Taxol Analogs, *Tetrahedron Lett.*, 1994, 35, 5543–5546.

(21) Klein, L. L.; Yeung, C. M.; Li, L.; Plattner, J. J., Synthesis of 9-Deoxotaxane Analogs, *Tetrahedron Lett.*, 1994, 35, 4707–4710.

(22) Ojima, I.; Park, Y. H.; Sun, C.-M.; Fenoglio, I.; Appendino, G.; Pera, P.; Bernacki, R. J., Structure-Activity Relationships of New Taxoids Derived from 14β-Hydroxy-10-deacetylbaccatin III, *J. Med. Chem.*, 1994, 37, 1408–1410.

(23) Datta, A.; Jayasinghe, L. R.; Georg, G. I., Internal Nucleophile Assisted Selective Deesterification Studies on Baccatin III, Synthesis of 2-Debenzoyl- and 4-Deacetylbaccatin III Analogs, *J. Org. Chem.*, 1994, 59, 4689–4690.

(24) Taxol: A Unique Antineoplastic Agent With Significant Activity in an Advanced Ovarian Epithelial Neoplasms, *Ann. Intern. Med*, 1989, 111, 273–279.

(25) Phase II Trial of Taxol, an Active Drug in the Treatment of Metastatic Breast Cancer, *J. Natl. Cancer Inst.*, 1991, 83, 1797–1805.

(26) Wani, et al., Plant Anti-Tumor Agents. VI. The Isolation and Structure of Taxol. A Novel Anti-Leukemic and Anti-Tumor Agent From Taxus Brevifolia, *J. Am. Chem. Soc.*, 1971, 93, 2325.

(27) R$_e$arrangement R$_e$actions of Taxanes: Structural Modifications of 10-Deacetylbaccatin III, *Tetrahedron*, 1992, 48, 6965–6974.

What is claimed is:

1. An antineoplastic compound, or a pharmaceutically acceptable salt thereof, comprising the general formula:

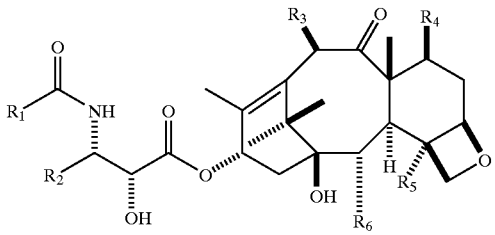

wherein $R_1$ is an aryl or substituted aryl; $R_2$ is an aryl or substituted aryl; $R_3$ is $OC(O)CH_3$; $R_4$ is OH; $R_5$ is S-methyldithiocarboxyoxy; and $R_6$ is $OC(O)R_g$, wherein $R_g$ is selected from the group consisting of alkyls, cycloalkyls, heterocycloalkyls, heterocycloaryls, alkenyls, alkynyls, aryls, and substituted aryls.

2. An antineoplastic compound, or a pharmaceutically acceptable salt thereof, comprising the general formula:

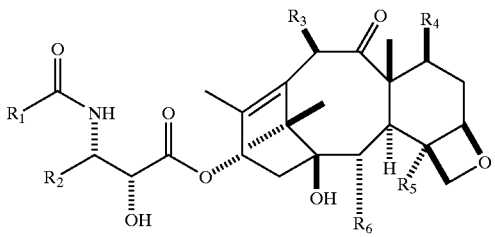

wherein $R_1$ is an aryl or substituted aryl; $R_2$ is an aryl or substituted aryl; $R_3$ is $OC(O)CH_3$; $R_4$ is OH; $R_5$ is S-methyldithiocarboxyoxy; and $R_6$ is selected from the group consisting of m-methoxybenzol, m-chlorobenzoyloxy and m-azidobenzoyloxy.

3. An antineoplastic compound, or a pharmaceutically acceptable salt thereof, comprising the general formula:

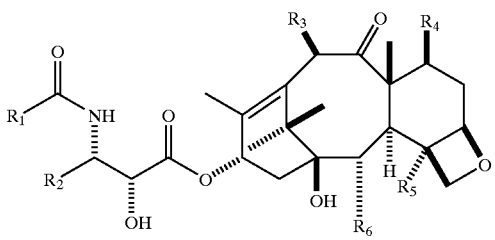

wherein $R_1$ and $R_2$ are phenyl; $R_3$ is $OC(O)CH_3$; $R_4$ is OH; $R_5$ is cyclopropylcarbonyloxy; and $R_6$ is 2,4-difluorobenzoyloxy.

* * * * *

UNITED STATES PATENT AND TRADEMARK OFFICE
CERTIFICATE OF CORRECTION

PATENT NO. : 6,476,242 B1
DATED : November 5, 2002
INVENTOR(S) : David George Ian Kingston et al.

It is certified that error appears in the above-identified patent and that said Letters Patent is hereby corrected as shown below:

Title page,
Item [56], References Cited, OTHER PUBLICATIONS
"Kurt A. Neidigh et al." should read -- Kurt A. Neidigh et al., --; and "Mahendra D. Chordia et al." should read -- Mahendra D. Chordia et al., --.

Column 2,
Line 5, "(20-21and" should read -- (20-21) and --;
Line 11, "dicyclhexy-" should read -- dicyclohexy- --; and
Line 33, "baccatin m" should read -- baccatin III --.

Column 3,
Line 26, "-deacety14-'" should read -- -deacetyl-4- --; and
Line 27, "pro" should read -- procedures for preparing these --.

Column 11,
Line 26, "(1986)" should read -- (1986). --.

Column 12,
Line 43, "-Butyldimethylsill-" should read -- -Butyldimethylsilyl- --; and
Line 65, "-debezneoyl-" should read -- -debenzoyl- --.

Column 13,
Line 16, "-triethylsilypaclitaxel" should read -- -triethylsilylpaclitaxel --;
Line 19, " δ 0.23" should read -- δ-0.23--;
Line 39, "butyldimethyl silyl" should read -- butyldimethylsilyl --;
Line 61, "-Butyldimethysilyl" should read -- -Butyldimethylsilyl --;
Line 62, "triethysilyl-" should read -- triethylsilyl- --; and
Line 63, "mmol))" should read -- mmol) --.

Column 14,
Line 9, "-Butyldimethysilyl-" should read -- -Butyldimethylsilyl- --;
Line 49, "-Butyldimethysilyl-7-triethysilyl-" should read -- -Butyldimethylsilyl-7-triethylsilyl- --;
Line 50, "4-acylpactaxel" should read -- 4-acylpaclitaxel --; and
Line 60, "non polar" should read -- non-polar --.

UNITED STATES PATENT AND TRADEMARK OFFICE
CERTIFICATE OF CORRECTION

PATENT NO. : 6,476,242 B1
DATED : November 5, 2002
INVENTOR(S) : David George Ian Kingston et al.

It is certified that error appears in the above-identified patent and that said Letters Patent is hereby corrected as shown below:

Column 15,
Line 12, "(0.2" should read -- (0.1 --;
Line 27, "-triethylsilypaclitaxel" should read -- -triethylsilylpaclitaxel --; and
Line 57, "Butyldimethylsiyl-7-O-triethysilyl" should read -- Butyldimethylsilyl-7-O-triethylsilyl --.

Column 16,
Line 27, "Butyldimethysilyl-7-O-triethysilyl" should read --Butyldimethylsilyl-7-O-triethylsilyl --;
Line 45, "J 8.24 Hz," should read -- J=8.24 Hz, --;
Line 59, "azidobenzoil)" should read -- azidobenzoyl) --; and
Line 63, "azido benzoyl)-" should read -- azidobenzoyl)- --.

Column 17,
Line 15, "1H." should read --1H).--;
Line 18, "2'-tert-Butyldimethysilyl-7-O-triethysilyl-" should read -- 2'-O-tert-Butyldimethylsilyl-7-O-triethylsilyl --;
Line 55, "dimethyl acryloyl)" should read -- dimethyl-acryloyl) --; and
Line 56, "deacety14-" should read -- deacetyl-4- --.

Column 18,
Line 1, "Butyldimethysilyl-7-O-Triethysilyl" should read -- Butyldimethylsilyl-7-O-triethylsilyl --;
Line 34, "Butyldimethysilyl-7-O-triethysilyl" should read -- Butyldimethylsilyl-7-O-triethylsilyl --;
Line 36, "Butyldimethylsily" should read -- Butyldimethylsilyl --; and
Line 51, "-butoxy carbonyl)-" should read -- -butoxy-carbonyl)- --.

Column 19,
Line 19, "$C_{50}DH_{57}$" should read --$C_{50}H_{57}$ --;
Line 29, "dideacetyl" should read -- di-deacetyl --;
Line 30, "1H" should read --$^{1}H$ --;
Line 31, "δ1.11" should read -- δ, 1.11 --;
Line 43, "Butyldimethysilyl-7-O-triethysilyl" should read -- Butyldimethylsilyl-7-O-triethylsilyl --; and
Line 49, "(tert-butoxy carbonyl)" should read -- (tert-butoxycarbonyl) --.

UNITED STATES PATENT AND TRADEMARK OFFICE
CERTIFICATE OF CORRECTION

PATENT NO. : 6,476,242 B1
DATED : November 5, 2002
INVENTOR(S) : David George Ian Kingston et al.

It is certified that error appears in the above-identified patent and that said Letters Patent is hereby corrected as shown below:

Column 20,
Line 2, "(tert-butoxy carbonyl)" should read -- (tert-butoxycarbonyl)- --;
Line 13, "1.76 (s, 3H)," (second occurrence) should be deleted;
Line 55, "R$_e$naud," should read -- Renaud, --; and
Line 64, "Structure Activity" should read -- Structure Activity --.

Column 21,
Line 14, "R. H." should read -- R.H., --; and
Line 19, "K. A." should read -- K.A., --.

Column 22,
Line 5, R$_e$arrangement R$_e$actions" should read -- Rearrangement Reactions --.
Line 47, "m-methoxybenzol" should read -- m-methoxybenzoyl --.

Signed and Sealed this

Fifth Day of October, 2004

JON W. DUDAS
*Director of the United States Patent and Trademark Office*